United States Patent
Kirkham

(10) Patent No.: US 9,551,716 B2
(45) Date of Patent: Jan. 24, 2017

(54) METHOD FOR DIAGNOSIS AND PROGNOSIS OF CHRONIC OBSTRUCTIVE PULMONARY DISEASE (COPD)

(71) Applicant: Paul Archibald Kirkham, Cranleigh (GB)

(72) Inventor: Paul Archibald Kirkham, Cranleigh (GB)

(73) Assignee: Paul Archibald Kirkham, Cranleigh, Surrey (GB)

( * ) Notice: Subject to any disclaimer, the term of this patent is extended or adjusted under 35 U.S.C. 154(b) by 0 days.

(21) Appl. No.: 14/890,948

(22) PCT Filed: May 12, 2014

(86) PCT No.: PCT/GB2014/051444
§ 371 (c)(1),
(2) Date: Nov. 13, 2015

(87) PCT Pub. No.: WO2014/184527
PCT Pub. Date: Nov. 20, 2014

(65) Prior Publication Data
US 2016/0097778 A1    Apr. 7, 2016

(30) Foreign Application Priority Data

May 13, 2013 (GB) .................................. 1308516.2

(51) Int. Cl.
*G01N 33/68* (2006.01)
*C07K 16/42* (2006.01)

(52) U.S. Cl.
CPC ........ *G01N 33/6854* (2013.01); *C07K 16/4241* (2013.01); *G01N 33/6893* (2013.01); *G01N 2333/47* (2013.01); *G01N 2500/00* (2013.01); *G01N 2800/122* (2013.01); *G01N 2800/52* (2013.01)

(58) Field of Classification Search
None
See application file for complete search history.

(56) References Cited

PUBLICATIONS

Kirkham et al., "Oxidative Stress-Induced Antibodies to Carbonyl-Modified Protein Correlate With Severity of Chronic Obstructive Pulmonary Disease," American Journal of Respiratory and Critical Care Medicine 184(7):796-802 (2011).
Packard et al., "COPD is Associated With Production of Autoantibodies to a Broad Spectrum of Self-Antigens, Correlative With Disease Phenotype," Immunologic Research 55:48-57 (2013).
Burcham et al., "Toxicity of Smoke Extracts Towards A549 Lung Cells: Role of Acrolein and Suppression by Carbonyl Scavengers," Chemico-Biological Interactions 183(3):416-424 (2010).
Brusselle et al., "Lymphoid Follicles in (Very) Severe COPD: Beneficial or Harmful?," European Respiratory Journal 34(1):219-230 (2009).
International Search Report and Search Report corresponding to PCT/GB2014/051444 (mailed Sep. 18, 2014).

*Primary Examiner* — Jacob Cheu
(74) *Attorney, Agent, or Firm* — LeClairRyan, a Professional Corporation

(57) ABSTRACT

A method for aiding in categorizing or determining prognosis in a subject with COPD, or in selecting a therapeutic strategy for a subject with COPD, or in monitoring disease progression or assessing effectiveness of a treatment regime for COPD, the method comprising the step of assessing the antibody response to carbonylated vimentin in a sample obtained from the subject. The method may further comprise the step of selecting a treatment regime making use of the information on the antibody response to carbonylated vimentin in the sample. The step of assessing of the antibody response to carbonylated vimentin may comprise the step of determining the ratio of IgG to IgM in the antibody response to carbonylated vimentin.

12 Claims, 10 Drawing Sheets

Figure 1:
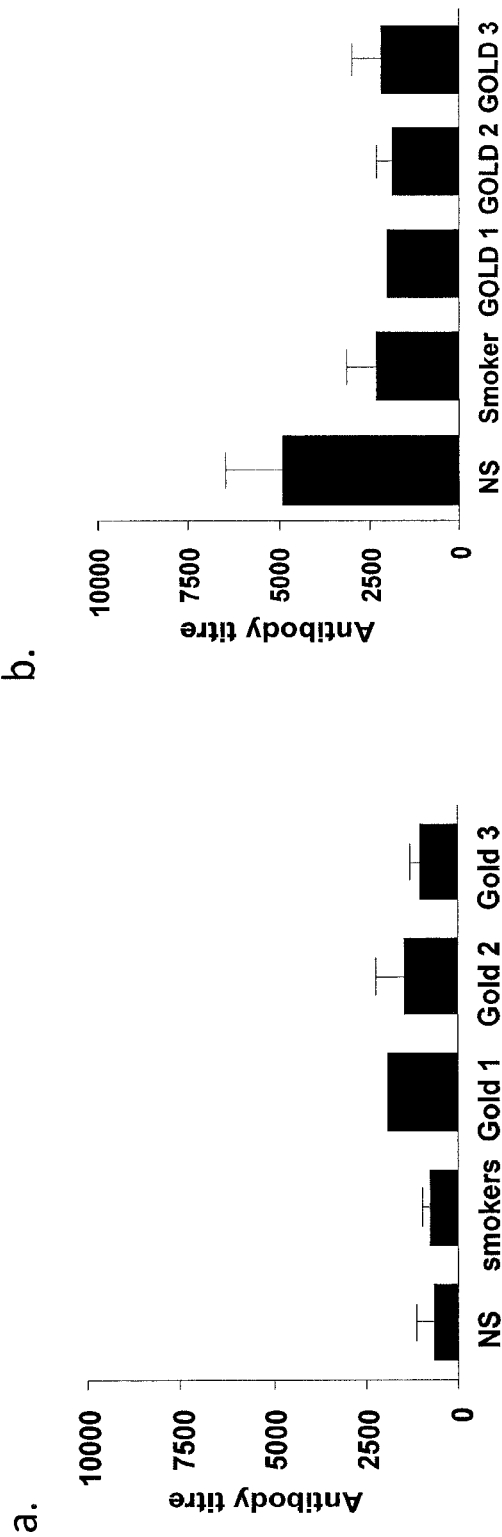

COPD severity as defined by Lung Function

| | 0: At Risk | I: Mild | II: Moderate | III: Severe | IV: Very Severe |
|---|---|---|---|---|---|
| Characteristics | • Chronic Symptoms<br>• Exposure to risk factors<br>• Normal spirometry | • $FEV_1/FVC < 70\%$<br>• $FEV_1 \geq 80\%$<br>• With or without symptoms | • $FEV_1/FVC < 70\%$<br>• $50\% \leq FEV_1 < 80\%$<br>• With or without symptoms | • $FEV_1/FVC < 70\%$<br>• $30\% \leq FEV_1 < 50\%$<br>• With or without symptoms | • $FEV_1/FVC < 70\%$<br>• $FEV_1 < 30\%$ or $FEV_1 < 50\%$ predicted plus chronic respiratory failure |

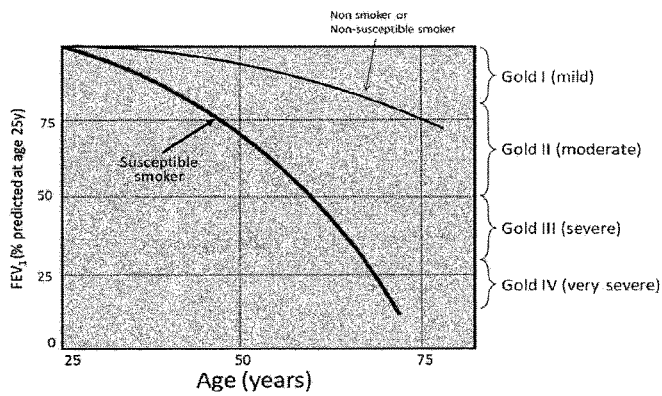

Definitions:
FVC = Forced vital capacity – total volume of air forcibly expelled form the lungs FEV1 = Volume of air expelled in 1 second

*Global Initiative for Chronic Obstructive Lung Disease (GOLD) 2008 update http://www.goldcopd.com/*

Figure 7

METHOD FOR DIAGNOSIS AND PROGNOSIS OF CHRONIC OBSTRUCTIVE PULMONARY DISEASE (COPD)

This application is a national stage application under 35 U.S.C. §371 of PCT Application No. PCT/GB2014/051444, filed May 12, 2014, which claims the priority benefit of Great Britain Application No. 1308516.2, filed on May 13, 2013.

The present invention relates to assessment and treatment of chronic obstructive pulmonary disease (COPD).

Chronic obstructive pulmonary disease (COPD) is a lung disease characterised by chronic airway inflammation and pulmonary emphysema resulting in airways limitation that is not fully reversible. The inflammatory response increases with severity of disease but responds poorly to treatment and while glucocorticoid steroids have proved highly effective anti-inflammatory drugs for the treatment of asthma, they are of limited therapeutic value in COPD due to reduced patient sensitivity to them.

While COPD pathogenesis has historically been viewed in the context of an aberrant innate response, there is increasing evidence indicating the involvement of the adaptive immune system. CD8 and CD4 T cells and B cells are detected in increased numbers in the small airways and lung tissue of subjects with the disease and lymphoid follicles have also been noted (Saetta, Di Stefano et al. 1998; Hogg, Chu et al. 2004; Sullivan, Simonian et al. 2005; van der Strate, Postma et al. 2006; Brusselle, Demoor et al. 2009)

However the nature of the antigen or antigens driving this specific immune response remains unclear. In common with other chronic inflammatory diseases, COPD has hallmarks of autoimmune dysfunction; and self-antigens, such as highly abundant structural proteins, either in native conformation or chemically or enzymatically altered in some way are a potential source. Antibodies against pulmonary epithelial cells (Kuo, Chang et al. 2010) endothelial cells (Feghali-Bostwick, Gadgil et al. 2008; Kirkham, Caramori et al. 2011) and extracellular matrix proteins such as elastin (Lee, Goswami et al. 2007) and collagen (Rinaldi, Lehouck et al. 2012) have been reported.

Exposure to reactive oxygen species (ROS) from tobacco smoke, industrial air pollution or organic combustion products, such as indoor cooking fires, are recognised as the biggest risk factors for developing COPD affecting millions of people worldwide. However, not all individuals exposed to these risk factors will go on to present with symptoms. Interestingly, lung inflammation persists even after cessation of smoking, suggesting that inflammation is driven by some factor beyond direct smoke exposure. The components within organic combustion products such as tobacco smoke, or the products of oxidative damage to tissues, such as lipid peroxidation, have been shown to readily modify proteins directly (eg. reactive carbonyl products present are capable of irreversibly modifying proteins in vitro and in vivo (Cerami, Founds et al. 1997; Nicholl and Bucala 1998; Nicholl, Stitt et al. 1998; Negre-Salvayre et al. 2008; Burcham et al. 2010) or promote the release of enzymes that may (eg. citrullination (Makrygiannakis, Hermansson et al. 2008), the enzymatic conversion of arginine residues in proteins to citrulline). Modifications of this nature can result in sufficient conformational change to render the protein potentially immunogenic, i.e. generating "neo-antigens" creating what were previously inert "self" proteins into effective auto-antigens thereby helping to drive an autoimmune pathology which may in part be responsible for the ensuing lung destruction observed in COPD.

Forced expiratory volume in one second (FEV1) is currently the most frequently used measurement of COPD disease severity and progression, but does not correlate well with symptoms and other disease markers. COPD severity is typically classified on the GOLD scale as GOLD1 (mild), GOLD2 (moderate) or GOLD3 (severe) or GOLD4 (very severe). See for example *Global Strategy for the Diagnosis, Management and Prevention of COPD*, Global Initiative for Chronic Obstructive Lung Disease (GOLD) 2013. http://goldcopd.org/.

We have surprisingly found a significant difference in antibody response, particularly class of antibody response, to carbonylated vimentin (but not other abundant structural proteins/modifications investigated) in patients with different COPD status. We consider that antibody response, particularly the class of antibody response and importantly the ratio of the response between these antibody classes to carbonylated vimentin to represent a prognostic and predictive factor in COPD, and a therapeutic target for COPD.

The listing or discussion of an apparently prior-published document in this specification should not necessarily be taken as an acknowledgement that the document is part of the state of the art or is common general knowledge.

Any document referred to herein is hereby incorporated by reference in its entirety.

A first aspect of the invention provides a method for aiding in categorising or determining prognosis in a subject with COPD, or in selecting a therapeutic strategy for a subject with COPD, or in monitoring disease progression or assessing effectiveness of a treatment regime for COPD, the method comprising the step of assessing the antibody response to carbonylated vimentin in a sample obtained from the subject. The method may further comprise the step of selecting a treatment regime making use of the information on the antibody response to carbonylated vimentin in the sample.

Typically the step of assessing of the antibody response to carbonylated vimentin comprises the step of determining the ratio of IgG to IgM in the antibody response to carbonylated vimentin. The ratio of IgG1 to IgM in the antibody response to carbonylated vimentin may alternatively or in addition be determined. The step of determining the ratio of IgG or IgG1 to IgM in the antibody response to carbonylated vimentin may typically comprise determining the level of IgM antibody and IgG or IgG1 antibody to carbonylated vimentin.

The ratio of IgG or IgG1 to IgM may of course be determined or expressed alternatively as the ratio of IgM to IgG or IgG1 as both reflect the same underlying relationship. The numerical values and the direction in which they vary will of course be inverted if expressed instead as the ratio of IgM to IgG or IgG1 instead of the ratio of IgG or IgG1 to IgM.

It will be appreciated that assessing the antibody response to carbonylated vimentin, optionally (for example) determining the ratio of IgG to IgM in the antibody response to carbonylated vimentin, optionally determining the ratio of IgG1 to IgM in the antibody response to carbonylated vimentin, may in itself allow categorising or determining prognosis in a subject with COPD, or selection of a therapeutic strategy for a subject with COPD; or more typically it may be used by the clinician as an aid in categorising or determining prognosis or selection of a therapeutic strategy.

For example, it is useful if the clinician undertakes lung function assessment, for example as specified by the GOLD guidelines and/or assessment of the degree of lung destruction, for example by CT scan. See Examples 1 and 3, for example, for illustration of typical patient assessment parameters. It will be appreciated that the clinician will wish to take in to account these or other factors, as well as consider the antibody response to carbonylated vimentin, for example the ratio of IgG to IgM in the antibody response to carbonylated vimentin, before categorising or determining prognosis or selection of a therapeutic strategy.

The GOLD assessment system will be well known to those skilled in the art. See the GOLD guidelines referenced above. See also FIG. 7 for a summary.

Determination of the antibody response to carbonylated vimentin, for example the ratio of IgG (or IgG1) to IgM in the antibody response to carbonylated vimentin in the sample will be useful to the clinician in determining how to manage the COPD in the subject. For example, since an high ratio of IgG (or IgG1) to IgM (for example an IgG:IgM ratio above 4 or 4.5, for example a ratio of 5 or more or 6 or more) is considered to be associated with more advanced disease (GOLD2 or GOLD3), the clinician may use the information concerning the antibody response to carbonylated vimentin, for example the ratio of IgG (or IgG1) to IgM in the antibody response to carbonylated vimentin, to facilitate decision making regarding treatment of the subject. Thus, for example, if the ratio of IgG (or IgG1) to IgM is low (for example an IgG:IgM ratio of 4 or less, for example 3.5 or less) and is therefore indicative of a lower probability of more advanced COPD (GOLD2 or GOLD3) being present, unnecessary treatments and/or monitoring may be avoided. Similarly, if (for example) the ratio of IgG (or IgG1) to IgM is high and therefore indicative of a higher probability of more advanced COPD (GOLD2 or GOLD3) being present, a wider range of therapeutic interventions may be more appropriate. Even if it is not appropriate to alter the type of therapy carried out, determining whether the ratio of IgG (or IgG1) to IgM is high and therefore indicative of a higher probability of more advanced COPD (GOLD2 or GOLD3) being present, may help the clinician to decide whether the patient needs more regular monitoring (for example more frequent visits to the clinician in order to assess disease progression or effectiveness of therapeutic intervention) or not.

The clinician may use the information concerning the antibody response to carbonylated vimentin, for example the ratio of IgG (or IgG1) to IgM in the antibody response to carbonylated vimentin, to facilitate decision making regarding treatment of an exacerbation in the subject. High IgG/IgM ratio are considered to indicate the onset of a mechanism associated with lung destruction. Therefore in high IgG:IgM subjects, additional therapies on top of the antiobiotics needed to treat the exacerbation or even alternative therapies may be required/selected to tackle both the exacerbation and the altered autoimmune state. These additional or alternative therapies may be immunomodulatory/immunosuppressive as well as complement cascade inhibitors in order to dampen down the innate and acquired immunity arms of the destructive autoimmune response. Examples of such therapies will be well known to those skilled in the art and are indicated below. In low IgG:IgM subjects, such additional or alternative therapies may not be required/ selected.

Further therapies that may be useful may include the following, as also discussed further below: antioxidant treatment (for example n-acetyl cysteine Biswas S, Hwang J, Kirkham P A and Rahman I (2012) Therapeutic intervention for Oxidative and Carbonyl stress in Respiratory disease. Curr Med Chem—EPub ahead of print( ); or anticarbonyls (for example metformin; AGE compounds; see also classes of compounds and particular compounds mentioned in Negre-Salvayre, A., C. Coatrieux, et al. (2008). "Advanced lipid peroxidation end products in oxidative damage to proteins. Potential role in diseases and therapeutic prospects for inhibitors." British Journal of Pharmacology 153(1): 6-20; and see also classes of compounds and particular compounds Aldini et al (2007) Intervention Strategies to Inhibit Protein Carbonylation by Lipoxidation-Derived Reactive Carbonyls Medicinal Research Reviews 27(6), 817-868). See also compounds and treatments discussed in Example 5 below, to be published in the Journal Chest in July 2013, authors Kirkham and Barnes.

Determination of the antibody response to carbonylated vimentin, for example the ratio of IgG (or IgG1) to IgM in the antibody response to carbonylated vimentin in the sample is considered to be useful in monitoring disease progression or assessing effectiveness of a treatment regime. Thus, a change in the (anti-carbonylated vimentin) IgG:IgM ratio (for example) for a COPD GOLD1 subject from a "low" ratio to a "high" ratio (as indicated above) may provide an early indication (possibly alongside other assessments such as FEV1 and CT scans) of disease progression (which may indicate that the treatment regime should be stopped or changed, or (for example in the context of a clinical trial) not selected for further investigation). A change in the (anti-carbonylated vimentin) IgG:IgM ratio (for example) for a COPD GOLD2 or GOLD3 subject from a "high" ratio to a "low" ratio (as indicated above) may provide an indication (possibly alongside other assessments such as FEV1 and CT scans) of disease improvement (which may indicate that the treatment regime should be continued or (for example in the context of a clinical trial) selected for further investigation). Thus, assessment of the IgG:IgM ratio may be useful in monitoring disease progression and/or effectiveness of a treatment regime for that subject. It may also be useful in the context of a clinical trial in which the effectiveness of a treatment regime is being assessed for regulatory purposes, for example relating to marketing approval of a therapeutic agent or treatment regime, or relating to cost effectiveness/reimbursement assessments. Thus, the (anti-carbonylated vimentin) IgG:IgM ratio (for example) may be used as a biomarker or surrogate endpoint in a clinical trial relating to COPD.

The sample obtained from the subject may be any sample type in which antibody response can be determined. The sample may typically be a blood or serum sample but may be, for example, another body fluid or tissue, for example saliva or urine or sputum or tissue biopsy (eg lung), as well known to those skilled in the art.

Samples may be obtained from the subject or subjects (for example during a clinical trial of a particular therapeutic or treatment regime) when the subject first presents with possible COPD (or first enrolls in a trial, for example); at regular intervals thereafter (for example six monthly or yearly) or when there appears to be a change in the subject's disease. For example, a sample may be obtained from the subject when or shortly after the subject with COPD experiences an exacerbation The ratio of IgG (or IgG1) to IgM (in the antibody response to carbonylated vimentin) which is indicative of a high probability of more advanced COPD (GOLD2 or GOLD3 or GOLD4) being present may be defined as the increased (high) ratio present in at least a subset of known subjects with clinically confirmed COPD GOLD2, GOLD3 or GOLD4, compared with known corresponding subjects without clinically confirmed COPD, for example healthy non-smokers. The ratio of IgG to IgM in the antibody response to carbonylated vimentin may be, for example, at least 4 or 4.5, for example at least 5 or 6 in subjects with COPD GOLD2, GOLD3 or GOLD4. The ratio of IgG to IgM in the antibody response to carbonylated vimentin may be, for example, the decreased (low) ratio in subjects without COPD, or without GOLD2, GOLD3 or GOLD 4 COPD, for example in non-smokers, smokers or subjects with GOLD1 (but not GOLD2 or GOLD3 or GOLD4) COPD, and may be less than 4 or 3.5, for example less than 3.

The antibody response to carbonylated vimentin, optionally the ratio of IgG (or IgG1) to IgM in the antibody response to carbonylated vimentin, may be determined in a sample in any suitable way. Quantitative analysis by enzyme linked immunosorbent assays (ELISA) measurement or alternative immunological based assay formats may be used, as well known to those skilled in the art. For example, immunoblotting, immunohistochemical means, radioimmunoassay, ELISPOT are examples of techniques that may be used. Any other method which makes use of the immunological properties of antibodies or their sub-component fragments in order to facilitate assessment of antibody titre or immunoreactivity to carbonyl vimentin so as to allow the determination of the IgG/IgM or its inverse ratio may also be used. Anti-carbonyly Ab or its fragments may be quantitated using, for example, enzyme linked-, fluorochrome linked-, orradioisotope linked-secondary detection reagents For example, antibody response to carbonylated vimentin may be assessed using an ELISA assay using a carbonylated vimentin polypeptide as the target protein; and (for example) secondary antibodies specific for IgG (or IgG1) and IgM to determine the IgG (or IgG1) and IgM components. Examples of suitable reagents and analysis are provided in Example 1. Vimentin may be carbonylated by treatment with malondialdehyde (MDA) or any other reactive carbonyl or combination thereof, for example 4 hydroxynonenal, acrolein or methylglyoxal. Example 1 describes the preparation of a carbonylated vimentin polypeptide, for example. Sources of suitable reagents (for example Sigma Aldrich Inc) are also described in, for example, Kirkham et al (2011) Am J Respir Crit Care Med 184, 796-802.

Other assay formats may also be used, for example radioimmunoassay (RIA), immunoradiometric assays (IRMA) and immunoenzymatic assays (IEMA), including sandwich assays using monoclonal and/or polyclonal antibodies.

It may be useful for the assay to be in a format that can be used quickly and reliably in a point of care setting, for example used by a general practitioner or a nurse (for example a specialist COPD nurse) in a surgery setting or on a home visit; or in an emergency assessment or treatment centre. The assay may be in a format that can be used by the subject themselves, for example in their home, for example either purchased on their own initiative, or as part of the care programme agreed with health professionals. Alternatively, it may be useful for the assay to be in a format suitable for high throughput, for example a microchip based assay. Such a format may be particularly useful when the assessment is being made as part of assessing a therapeutic regime, for example as part of a clinical trial.

It is not considered necessary to distinguish antibodies that are only able to bind to carbonylated vimentin from antibodies that are able to bind to both carbonylated vimentin and also non-carbonylated vimentin. Thus, it is considered sufficient to assess antibodies that bind to carbonylated vimentin. Typically the carbonylated vimentin is native carbonylated vimentin ie not vimentin that has been deliberately denatured, for example by exposure to excessive heat or extremes of pH or salt concentration, as will be well known to those skilled in the art. The carbonylated vimentin used as target protein in the assessments of Example 1 is considered to be an example of native vimentin suitable for carrying out the present invention.

The vimentin used in Example 1 was checked using the Dinitrophenyhydrazine assay which tests for carbonyl modification of the protein (reference Kirkham et al 2011) but it was not considered that any other check on native structure or otherwise was relevant.

It will be appreciated that assessment of antibodies that bind to carbonylated vimentin may be assessed using a carbonylated fragment of vimentin. Suitable fragments may readily be determined by techniques well known to those skilled in the art. For example, the epsilon amino group on lysine is a suitable site for carbonylation, so long as the site is available for modification in vivo. Similarly, the alpha amino group on lysine or any other amino acid or peptide can also be carbonylated, if it is available for modification in vivo. Epitope mapping studies may be used in identifying particularly suitable fragments.

Vimentin sequences are well known and may be found at, for example,

| External Ids: | HGNC: 12692[1] | Entrez Gene: 7431[2] | Ensembl: ENSG00000026025[7] | OMIM: 193060[5] | UniProtKB: P08670[3] |
|---|---|---|---|---|---|
| IDs | OMIM: 193060 MGI: 98932 HomoloGene: 2538 http://en.wikipedia.org/wiki/GeneCards | | | | |

It is preferred that the carbonylated vimentin polypeptide is a carbonylated human vimentin polypeptide. It is preferred that the carbonylated human vimentin polypeptide is carbonylated full length human vimentin.

The methods of the invention also include the assessment of the said antibody response to carbonylated vimentin, optionally the ratio of IgG (or IgG1) to IgM in said antibody response to carbonylated vimentin, in test samples and their comparison in a control sample.

A further aspect of the invention provides a kit of parts useful for assessing COPD, for example in assessing severity of COPD, monitoring disease progression or assessing effectiveness of a treatment regime, comprising (1) an agent which is specifically capable of use in assessing the antibody response to carbonylated vimentin in a sample, optionally the ratio of IgG (or IgG1) to IgM in said antibody response to carbonylated vimentin. The kit may optionally be suitable as a point of care kit, for example may be configured to be able to provide a read-out in less than about 6, 3, 2 or 1 hours, for example in less than 30 minutes from commencing a particular assessment, for example from the taking of a sample from the subject. The kit may be configured to provide a read-out via a visual signal that can be interpreted without instrumentation; or may comprise instrumentation, software or instructions to transmit the read-out to a remote location.

The agent which is specifically capable of use in assessing the antibody response to carbonylated vimentin in a sample, optionally the ratio of IgG (or IgG1) to IgM in said antibody response to carbonylated vimentin, may be a carbonylated vimentin polypeptide, optionally supplied with or coated on a support (for example a microtiter plate or a microchip) suitable for performing an immune assay, for example an ELISA assay.

Preferably, the kit further comprises a control sample. The control sample may be a negative control (which may contain serum from a subject without COPD, with, for example, a low IgG:IgM ratio in the antibody response to carbonylated vimentin) or it may be a positive control (contains serum from a subject with COPD GOLD2, 3 or 4, known to have a high IgG:IgM ratio in the antibody response to carbonylated vimentin). The negative control may be serum dilution buffer, for example. The kit may contain both negative and positive controls. The kit may usefully contain controls of the antibodies reactive with carbonylated vimentin which correspond to different amounts such that a calibration curve may be made.

The kits usefully may contain controls and detection material, (for example, for immunohistochemistry, secondary antibodies labelled fluorophores, or enzymes, or biotin, or digoxygenin or the like). For immunoassays, additional components to the kit may include a secondary antibody or antibodies, for example to an antibody type, for example IgM or IgG (optionally labelled or attached to a support), and dilution and reaction buffers. Similar additional components may usefully be included in all of the kits of the invention.

A further aspect of the invention provides an agent which is specifically capable of use in assessing the antibody response to carbonylated vimentin in a sample, optionally the ratio of IgG (or IgG1) to IgM in said antibody response to carbonylated vimentin, for aiding in categorising or determining prognosis in a subject with COPD, or in selecting a therapeutic strategy for a subject with COPD, or in monitoring disease progression or assessing effectiveness of a treatment regime for COPD.

A further aspect of the invention provides the use of an agent which is specifically capable of use in assessing the antibody response to carbonylated vimentin in a sample, optionally the ratio of IgG (or IgG1) to IgM in said antibody response to carbonylated vimentin, in the manufacture of a medicament for aiding in categorising or determining prognosis in a subject with COPD, or in selecting a therapeutic strategy for a subject with COPD, or in monitoring disease progression or assessing effectiveness of a treatment regime for COPD.

The agent may be, for example, a carbonylated vimentin polypeptide, as discussed above.

If the subject's anti-carbonylated vimentin IgG:IgM ratio is high (as indicated above), then a selected treatment regime may incorporate one or more of immunomodulatory treatment (for example anti CD20; anti-IL17; complement inhibitors, for example considered to block antibody dependent complement mediated tissue destruction, for example Eculizumab, a humanized monoclonal antibody that inhibits complement factor C5, or further examples mentioned in Schrezenmeier & Höchsmann (2012) *Transfus Apher Sci.* 2012 February; 46(1):87-92. Drugs that inhibit complement. doi: 10.1016/j.transci.2011.11.012. Epub 2011 Dec. 13); antioxidant treatment (for example n-acetyl cysteine Biswas S, Hwang J, Kirkham P A and Rahman I (2012) Therapeutic intervention for Oxidative and Carbonyl stress in Respiratory disease. Curr Med Chem—EPub ahead of print( ); or anticarbonyls (for example metformin; AGE compounds; see also classes of compounds and particular compounds mentioned in Negre-Salvayre, A., C. Coatrieux, et al. (2008). "Advanced lipid peroxidation end products in oxidative damage to proteins. Potential role in diseases and therapeutic prospects for inhibitors." British Journal of Pharmacology 153(1): 6-20; and see also classes of compounds and particular compounds Aldini et al (2007) Intervention Strategies to Inhibit Protein Carbonylation by Lipoxidation-Derived Reactive Carbonyls Medicinal Research Reviews 27(6), 817-868). See also compounds and treatments discussed in Example 5 below, to be published in the Journal Chest in July 2013, authors Kirkham and Barnes.

Whilst not intending to be bound by theory, it is considered that the high IgG:IgM ratio may reflect an increase in potentially harmful anti-carbonylated vimentin IgG levels (for example an increase in IgG1 levels, which can lead to complement activation) and/or a decrease in potentially protective anti-carbonylated vimentin IgM levels. Thus, immunomodulatory treatments may be particularly useful in such subjects. Antioxidant or anticarbonyl treatment may also be particularly useful in such subjects as the high anti-carbonylated IgG:IgM ratios may indicate presence or susceptibility to oxidative stress/carbonylation conditions. Alternatively or in addition, one or more of these or other treatment regimes may be considered to be a relatively aggressive treatment regime (for example because there may be a slightly higher risk of side-effects), with the result that treatment may only or mainly be recommended in patients who have been assessed as having a higher risk of disease progression and/or higher likelihood of the treatment being beneficial, either or both of which may be on the basis of a high anti-carbonylated IgG:IgM ratio. The subject's IgG:IgM ratios (for example) may be monitored more frequently, for example every 1 to 2 months.

Selective/targeted use of intense support for smoking cessation or other interventions designed to modify population risk may also be indicated for a cohort of the population with a high IgG:IgM ratio.

If the subject's anti-carbonylated vimentin IgG:IgM ratio is low (as indicated above), then a selected treatment regime may be a less aggressive treatment regime. Typically the patient would be managed with best standard of care according to standardised criteria (see GOLD website indicated above). Examples may include watchful waiting. The subject's IgG:IgM ratios (for example) may be monitored less frequently, for example yearly.

A further aspect of the invention provides a method for treating a subject with COPD, the method comprising administering to the subject an anti-idiotypic antibody or antibody fragment directed to an anti-carbonylated vimentin antibody; or a non-complement-activating anti-carbonylated vimentin antibody or antibody fragment. Methods of preparing an anti-idiotypic antibody or antibody fragment will be well known to those skilled in the art. Likewise, non-complement-activating antibodies or antibody fragments will be well known to those skilled in the art, as will be methods of generating such antibodies able to bind to carbonylated vimentin. See, for example An et al (2009 November-December) MAbs. 2009 1(6): 572-579. PMCID: PMC2791314 IgG2m4, an engineered antibody isotype with reduced Fc function. See also Siberil et al (2007) Anal New York Acad Sci Vol 1110, p 497-506. See also Valim & Lachmann *Clin Exp Immunol.* 1991 April; 84(1):1-8. The effect of antibody isotype and antigenic epitope density on the complement-fixing activity of immune complexes: a systematic study using chimaeric anti-NIP antibodies with human Fc regions.

Whilst not intending to be bound by theory, it is considered that such agents may be effective in reducing damage, for example complement-mediated damage, that may be caused to endothelial cells as a consequence of anti-carbonylated vimentin antibodies, particularly when there is a high IgG:IgM ratio of anti-carbonylated vimentin antibodies.

Thus, the subject optionally is a subject for which the IgG:IgM ratio of anti-carbonylated vimentin antibodies has been determined to be high (as indicated above).

A further aspect of the invention provides an anti-idiotypic antibody or antibody fragment directed to an anti-carbonylated vimentin antibody; or a non-complement-activating anti-carbonylated vimentin antibody or antibody fragment for use in treating a subject with COPD; optionally a subject for which the IgG:IgM ratio of anti-carbonylated vimentin antibodies has been determined to be high.

A further aspect of the invention provides the use of an anti-idiotypic antibody or antibody fragment directed to an anti-carbonylated vimentin antibody; or a non-complement-activating anti-carbonylated vimentin antibody or antibody fragment in the manufacture of a medicament for treating a patient with subject with COPD; optionally a subject for which the IgG:IgM ratio of anti-carbonylated vimentin antibodies has been determined to be high.

It will be appreciated that antibody-like molecules may be used in the use, medicament or method of the inventions including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs.

In a further embodiment, the subject may be administered an additional anti-COPD agent or treatment, for example an immunomodulatory, anti-oxidant or anti-carbonyl agent as indicated above. The agents may be formulated or administered separately or together.

A further aspect of the invention provides a screening method for identifying a compound likely to be useful in treating COPD, the method comprising the step of determining the effect of a test compound on antibody response to carbonylated vimentin, optionally IgG:IgM ratio in said antibody response, in a sample from a subject receiving the test compound; and selecting a compound that positively modulates said antibody response, optionally reduces said IgG:IgM ratio, optionally from a high to a low level (as indicated above), or prevents or reduces an increase in said IgG:IgM ratio from a low level to a high level. The subject may be a human or may be a non-human animal. For example the ozone animal model described in Kirkham et al (2011) may be used. Suitable assays are as indicated above. The compound may be, for example, an immunomodulatory, anti-oxidant or anti-carbonyl compound.

The invention is now described in more detail by reference to the following, non-limiting, Figures and Examples.

FIGURE LEGENDS

FIG. 1. Autoantibody response against native and carbonyl-modified elastin. Serum was screened for reactivity toward native (a) or carbonyl-modified (b) elastin by ELISA and titres determined as detailed in Methods. Results are expressed as mean±SEM for each patient group. Statistical analysis was performed using the Kruskal-Wallis test, $p>0.05$.

Figure 2:
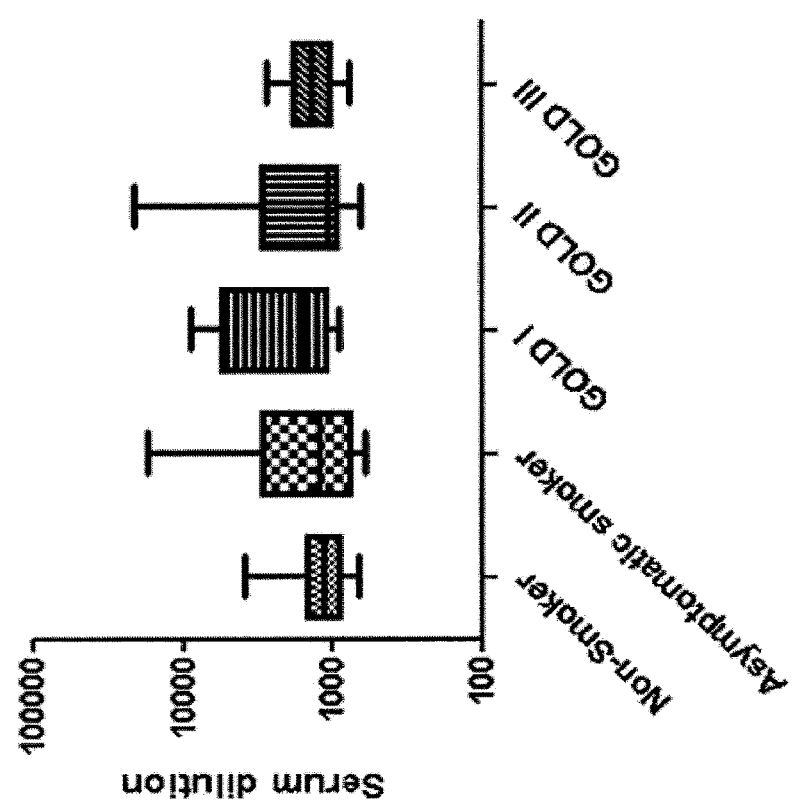

FIG. 2. Autoantibody response against carbonyl-modified collagen IV. Serum was screened for reactivity toward carbonyl-modified collagen V by ELISA and titres determined as detailed in Methods. Results are expressed as mean±SEM for each patient group. Statistical analysis was performed using the Kruskal-Wallis test, $p>0.05$.

Figure 3:
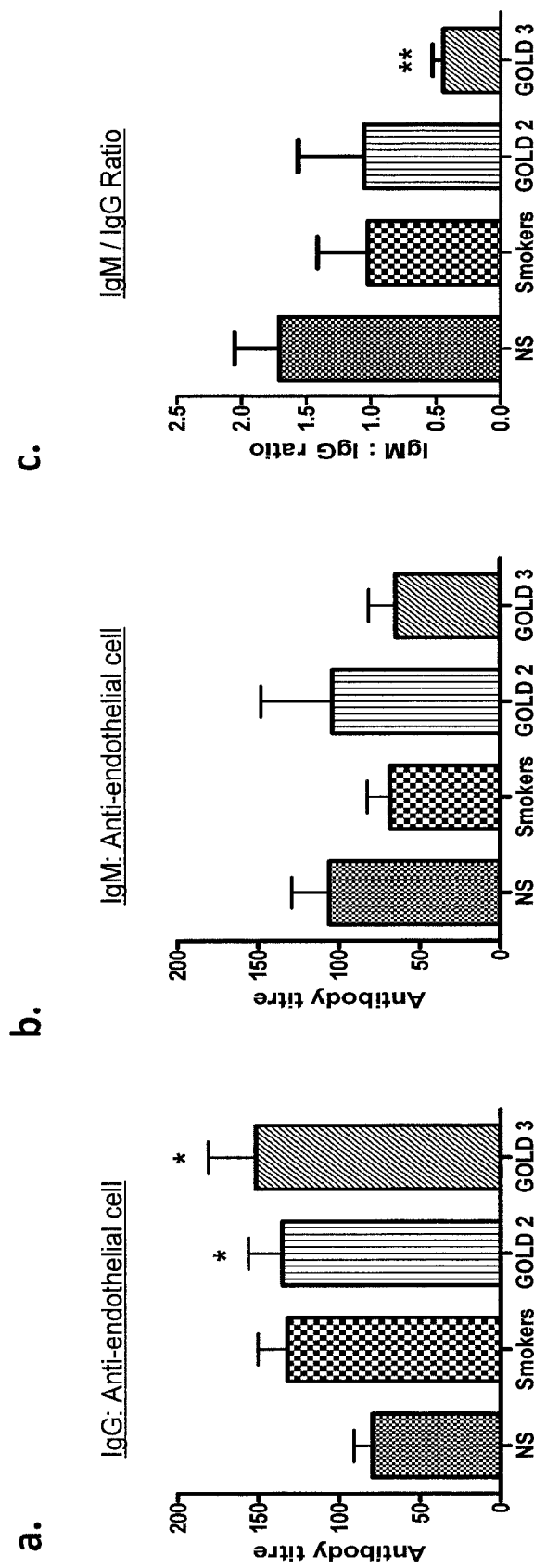

FIG. 3. Autoantibody response against endothelial cells Serum was screened for IgG (a) and IgM (b) immunoreactivity to whole endothelial cells by ELISA and titres determined as detailed in Methods. Results are expressed as mean±SEM for each patient group. IgM:IgG ratios were calculated and expressed as mean±SEM. Statistical analysis was performed using the Kruskal-Wallis test, $*p<0.05$, $**p<0.01$ compared to non-smokers.

Figure 4:
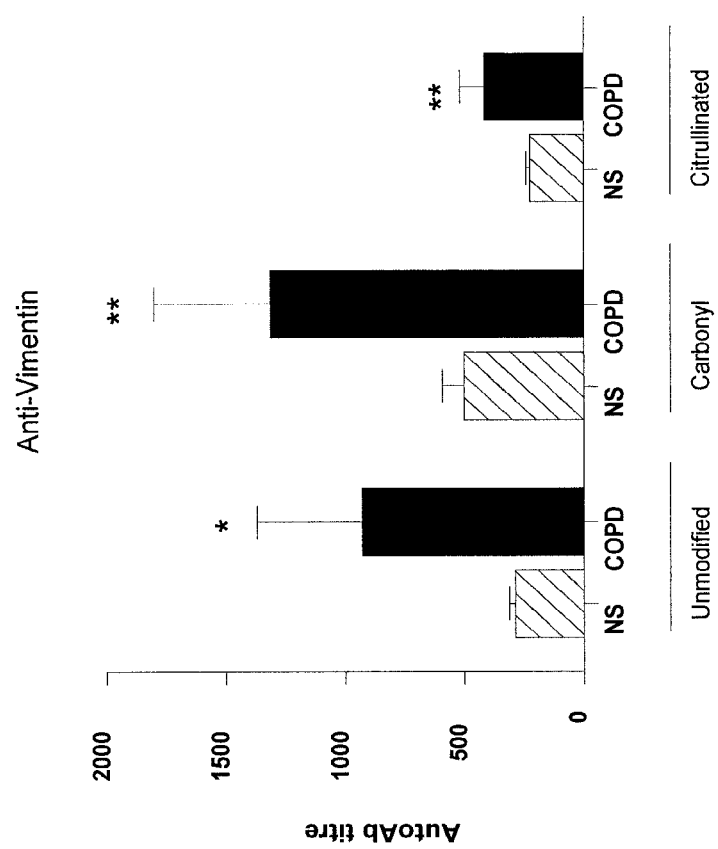

FIG. 4. Autoantibody response against native and modified vimentin. Serum was screened for immuno-reactivity toward native, carbonylated or citrullinated vimentin by ELISA and IgG titres determined as detailed in Methods. Results are expressed as mean titre±SEM for each patient group. Statistical analysis was performed using the Mann and Whitney U test, *: $p<0.05$, **: $p<0.01$ FIG. 5. Autoantibody response carbonyl-modified vimentin. Serum was screened for reactivity toward native, carbonylated vimentin by ELISA and titres determined as detailed in Methods. Results are expressed as mean titre±SEM for each patient group or the ratio of IgM.IgG±SEM. Statistical analysis was performed using the Kruskal-Wallis test (*: $p<0.05$, **: $p<0.01$ relative to non-smokers (NS); #: $p<0.05$, ###: $p<0.001$ relative to smokers)

Figure 6:
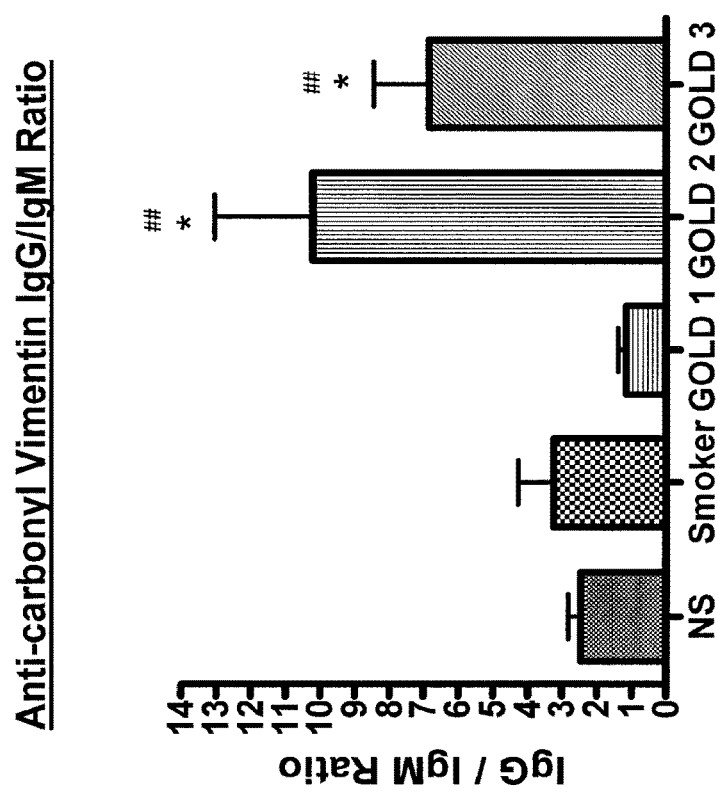

FIG. 6. IgG/IgM Autoantibody ratio to carbonyl-modified vimentin. Serum was screened for reactivity toward native, carbonylated vimentin by ELISA and titres determined as detailed in Methods. Results are expressed as mean titre±SEM for each patient group or the ratio of IgG:IgM±SEM. Statistical analysis was performed using the Kruskal-Wallis test (*: $p<0.05$, **: $p<0.01$ versus smoker; #: $p<0.05$, ##: $p<0.01$ versus non-smoker (NS))

FIG. 7: Figure Summarising GOLD assessment criteria.

Figure 8:
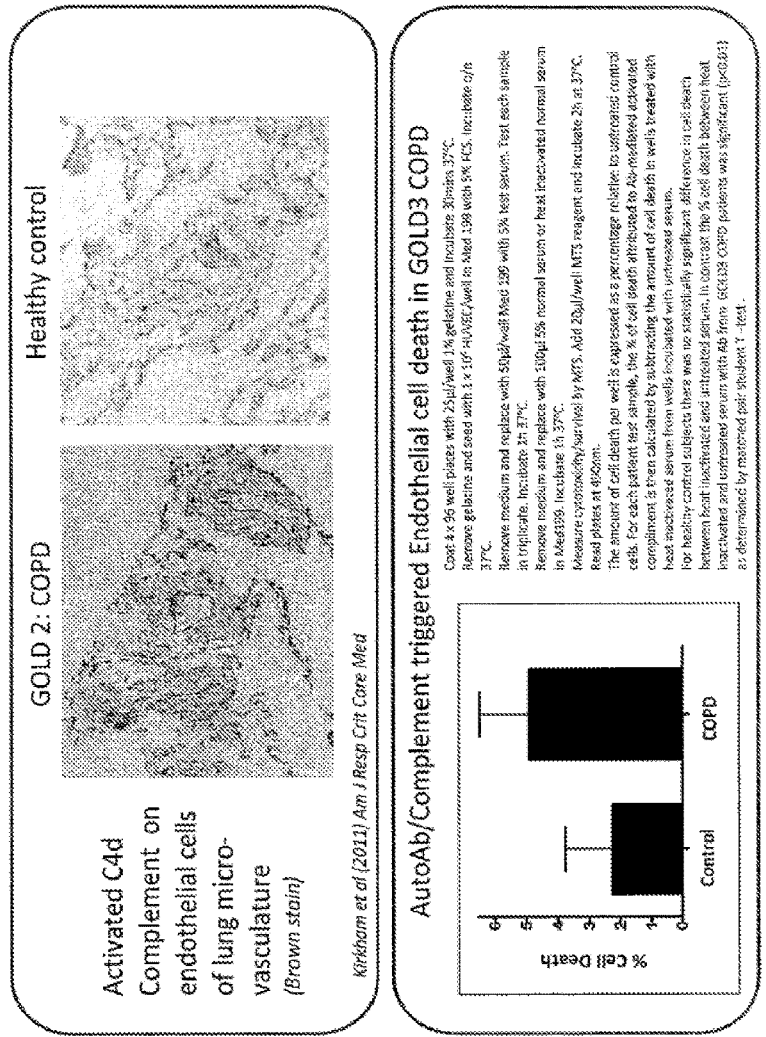
Figure 9:
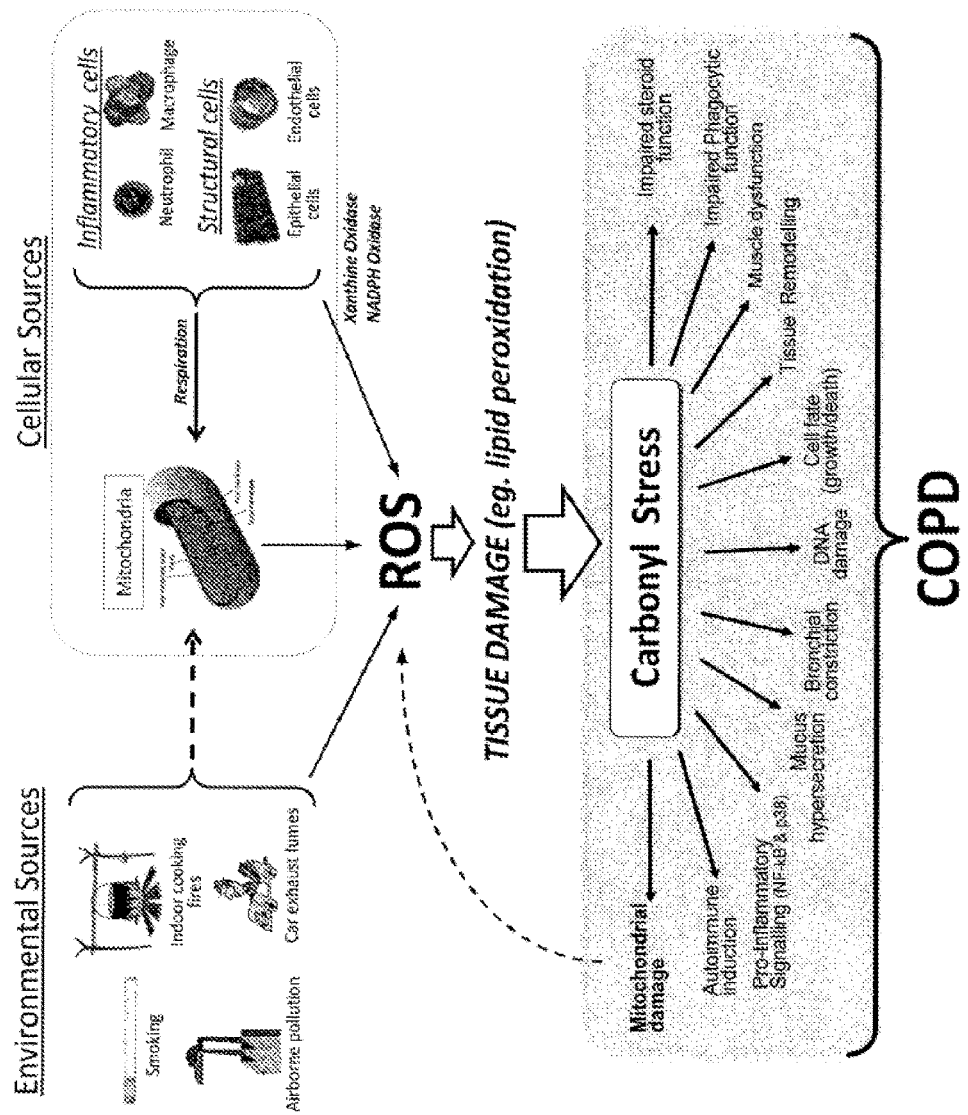

FIG. 8: Activated Complement deposition in COPD lungs & complement-mediated endothelial cell death FIG. 9 A mechanism for the development of COPD driven by oxidative stress through the formation of carbonyl stress. Oxidative stress from environmental and cellular sources causes tissue damage through lipid peroxidation and the oxidation of proteins and carbohydrates resulting in the formation of carbonyl stress. Carbonyl stress in turn causes non-enzymatic post-translational modifications on proteins which can alter protein function, as well as result in the formation of danger-associated molecular patterns (DAMPs) and neo-autoantigens. Importantly, damage to mitochondrial proteins by carbonyl stress only helps to drive further endogenous ROS production by the damaged mitochondria. Together these carbonyl-modified proteins help to drive the pathophysiological mechanisms associated with the development of COPD.

Figure 10:
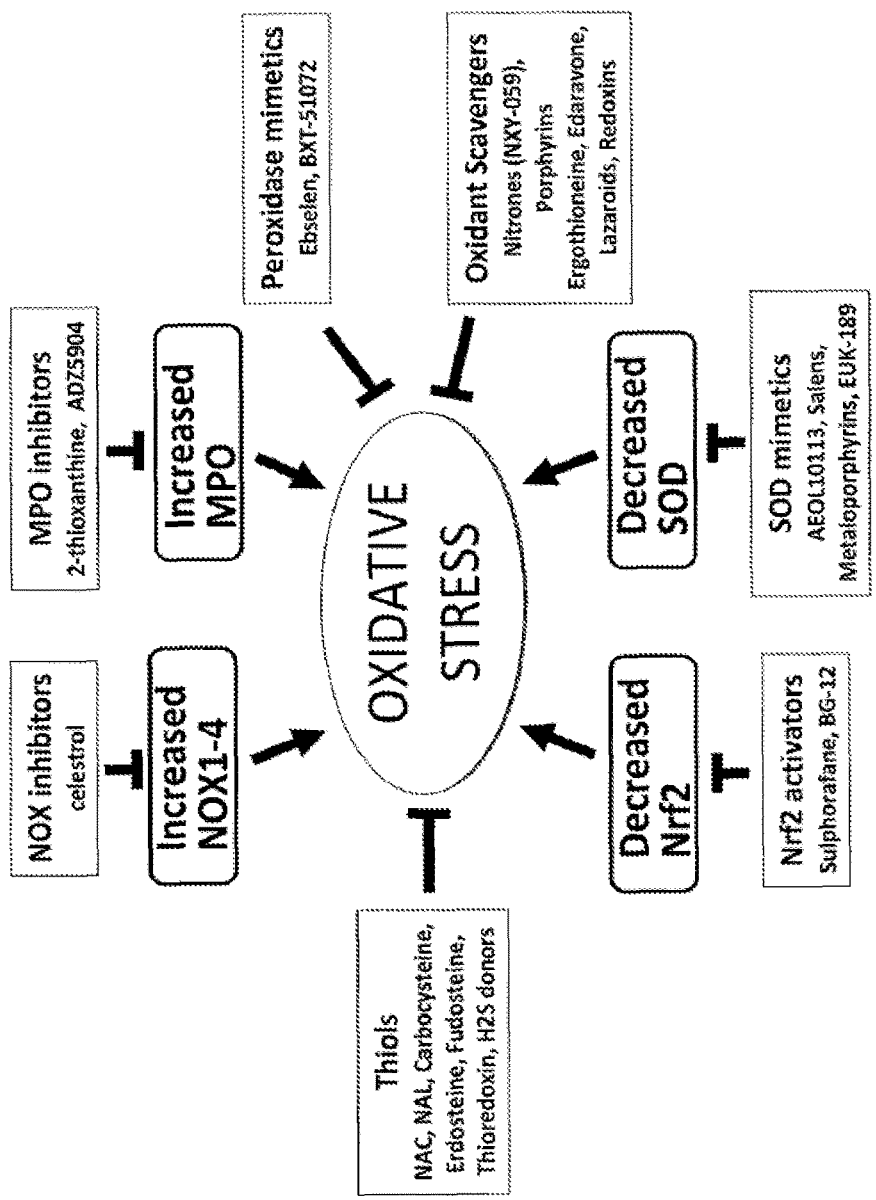

FIG. 10: Summary of the different therapeutic approaches to neutralize oxidative stress in COPD. Thiols, oxidant scavengers and peroxidase mimetics target and neutralize the oxidative stress directly. SOD mimetics and Nrf2 activators attempt to replenish the reduced SOD and Nrf2 activity that is absent in COPD. NADPH oxidase (NOX) and myeloperoxidase (MPO) inhibitors will neutralize and so reduce oxidative stress.

Example 1

Antibody Responses in COPD

Exposure to environmental ROS/RNS, such as tobacco smoke, is recognised as the single biggest risk factor for developing COPD, although not all smokers will go on to present with symptoms. Lung inflammation persists even after cessation of smoking, suggesting that inflammation is driven by some factor beyond direct smoke exposure. Tobacco smoke is a complex mixture of more than 5000 chemicals (Talhout, Schulz et al. 2011) including many known to be toxic and/or carcinogenic. In addition the components of tobacco smoke or oxidative damaged to tissues, such as lipid peroxidation, have been shown to readily modify proteins directly (eg. reactive carbonyl products present are capable of irreversibly modifying proteins in vitro and in vivo (Cerami, Founds et al. 1997; Nicholl and Bucala 1998; Nicholl, Stitt et al. 1998; Negre-Salvayre et al. 2008; Burcham et al. 2010) or promote the release of enzymes that may (eg. citrullination (Makrygiannakis, Hermansson et al. 2008), the enzymatic conversion of arginine residues in proteins to citrulline). Modifications of this nature resulting in sufficient conformational change may render the protein potentially immunogenic, i.e. generating "neo-antigens".

We wished to determine if such modifications could promote detectable immune responses and in this Example we report on our findings looking at antibody responses to several abundant structural proteins in both native form and following modification by carbonylation and also to endothelial cells.

Methods

Patients and Sera

Subjects were recruited from the Section of Respiratory Medicine of the University Hospital of Ferrara, Italy, with approval by the local Ethics Committee. Written informed consent was obtained from each participant in accordance with the principles outlined in the Declaration of Helsinki. Venous peripheral blood was collected, processed and stored as described in Kirkham et at 2011 (Kirkham, Caramori et al. 2011). Pulmonary function tests were performed as described in Varani et al 2006 (Varani, Caramori et al. 2006) according to published guidelines. Predicted values for the different measures were calculated from the regression equations published by Quanjer (Waalkens, Merkus et al. 1993). COPD was defined according to international guidelines (post-bronchodilator FEV1/FVC ratio <70%) and the severity of COPD was classed according to current GOLD criteria (http://www.goldcopd.org/). Subject details are summarised in Table 1.

Source of Proteins

Full-length native recombinant vimentin was a kind gift from Professor Marlene Rose (Harefield Hospital, England). Elastin and collagen IV were purchased from Sigma.

Citrullination of Vimentin

Vimentin was citrullinated according to the method of Bang et al 2007 (Bang, Egerer et al. 2007). Briefly, vimentin was reacted for 3 hours at 55° C. with 40 units of rabbit muscle peptidyl arginine deiminase (PAD; Sigma) per milligram of protein in a buffer containing 50 mM Tris HCl, 5 mM CaCl2, 2 mM DTT, 0.5 mM EDTA, 5 mM methylammonium chloride, pH 7.4. EGTA (pH 8.0) to a final concentration of 50 mM was added to stop the reaction.

Malondialdehyde Modification of Proteins

Malondialdehyde modification was performed using a modification of that described by Haberland et at 1982 (Haberland, Fogelman et al. 1982). Briefly, a 0.2M stock solution of MDA was generated by mixing 162 µl of malonaldehyde bis(dimethyl acetal) (Alpha Diagnostics Inc) with 200 µl of 2M HCl. After incubation at room temperature for 15 min, 4.8 ml phosphate buffer (pH 6.4) was added and the solution neutralised with NaOH.

Equal volumes of elastin or vimentin at 1 mg/ml were mixed with the activated MDA solution and incubated 24 h 37° C. Unreacted MDA was removed from solution by dialysis against PBS. For modification of collagen, protein was bound to microtitre plates and then incubated for 24 h at 37° C. with 0.1M activated MDA. MDA solution was aspirated and the plates were washed twice with PBS.

ELISA Protocol

Patient serum was screened for antibodies against native or modified proteins by ELISA using 96-well Nunc Maxisorb immunoplates coated with 0.1 µg/well target protein. Serial dilutions of serum were added and bound antibodies were assessed for IgG or IgM using appropriate secondary antibodies.

Anti-Endothelial Cell ELISA

A live cell ELISA was developed using human umbilical vein endothelial cell monolayers to screen patient sera for reactivity to whole endothelial cells. Cells were seeded overnight on gelatine coated microtitre plates, washed and exposed to serial dilutions of test serum. Bound IgG and IgM was assessed using appropriate secondary antibodies.

Statistical Analysis

GraphPad Prism was used to perform all statistical analyses. Antibody titres are expressed as mean±SEM. Mann-Whitney and Kruskal-Wallis tests was used to determine differences between groups and p values <0.05 were considered statistically significant.

Results

No Autoantibody Response Against Native and Carbonyl-Modified Elastin

Since the initial report detailing anti-elastin autoimmunity in smoke induced emphysema (Lee, Goswami et al. 2007), several groups have looked but been unable to confirm these results (Cottin, Fabien et al. 2009; Greene, Low et al. 2010; Brandsma, Kerstjens et al. 2011; Rinaldi, Lehouck et al. 2012). We screened our cohort for antibodies to native and carbonylated elastin (FIG. 1). There was no statistically significant difference in antibody titre between any of the groups to either the unmodified or carbonyl-modified antigen.

Antibody Response to Collagen IV

In-plate MDA-modified type IV collagen coated plates were used to screen patient serum for antibody response to this antigen (FIG. 2). No statistically significant difference in antibody titre was detected between any of the groups.

Increased Anti-Endothelial IgG Autoantibody Response and Reduced IgM/IgG Ratio in COPD Patient serum was tested for reactivity to endothelial cells in a live cell ELISA using human umbilical vein endothelial cells (FIG. 3). IgG autoantibody levels against endothelial cells were significantly elevated in subjects with COPD compared with healthy non-smokers and also elevated in asymptomatic smokers (FIG. 3a). There was no statistical difference in IgM titre between the groups (FIG. 3b). The IgM to IgG ratio was highest in non-smokers, falling in asymptomatic smokers and COPD, with the lowest ratio in the GOLD 3 group (FIG. 3c).

Autoantibody Response Against Native and Modified Vimentin

Antibodies to mutated citrullinated vimentin have both diagnostic and prognostic value in rheumatoid arthritis, making this an interesting antigen to investigate in other chronic inflammatory settings. Serum samples were tested for antibodies to native vimentin and citrullinated and carbonylated vimentin (FIG. 4). There was a statistically significant increase in antibody titre in COPD positive samples compared to non-smokers against all three antigens, indicative of an immune response against both native and modified vimentin.

Figure 5:
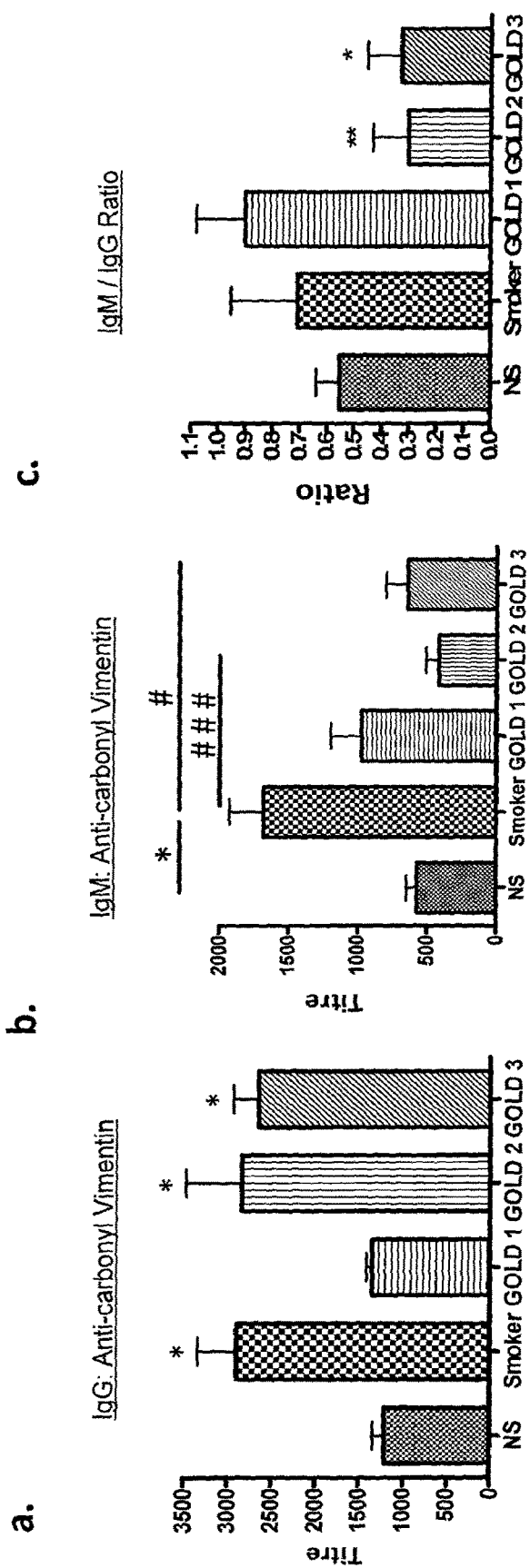

Further analysis of the antibody response to carbonylated vimentin (FIGS. 5 and 6) revealed elevated IgG titres in both asymptomatic smokers and individuals with moderate and severe COPD (GOLD 2 and 3) compared to non-smokers (FIG. 5a). IgG titres of individuals with mild COPD (GOLD 1) were not significantly different to non-smokers. In contrast, while IgM titres in asymptomatic smokers were elevated compared to non-smokers (approximately three-fold), there was no statistically significant difference in titre between non-smokers and patients with COPD (FIG. 5b). Finally, we looked at the ratio of both IgM to IgG (FIG. 5c) and of IgG to IgM (FIG. 6). There was no statistically significant difference between asymptomatic smokers or GOLD 1 and non-smokers for both ratios, IgM/IgG (FIG. 5c) or for IgG/IgM (FIG. 6); however the ratio for GOLD 2 and 3 was significantly different compared to non-smokers in both cases (FIG. 5c and FIG. 6). Moreover in the case of the ratio of IgG to IgM not only was there a markedly significant increase in the ratio for GOLD 2 and 3 relative to non-smokers, but this ratio was also significantly increased relative to asymptomatic smokers (FIG. 6). These results indicate that by considering both IgM and IgG responses together, antibody responses to carbonylated vimentin could be used to identify more advanced COPD.

The IgM/IgG and IgG/IgM ratios may not precisely reciprocate each other in FIG. 5c and FIG. 6. This is considered to be because the ratios are calculated for each patient separately and then plotted as the mean ratio+/−SEM for each disease group of patients. Hence each group will not necessarily mirror each other on the respective IgG/IgM and IgM/IgG ratios. If as an alternative, each group were as a whole for say IgG/IgM and then reciprocated to get the mirrored IgM/IgG ratio, then you would get the mirror image. As there are small numbers of patients in each group (refer to table 1) then the errors due to variability will be greater than if there were a larger number of patients. As the patient number increases so the variability should become less and the mean of the individual patient ratios should begin to mirror each other more closely.

| | IgG | IgM | Ratio IgG:IgM |
|---|---|---|---|
| Non-smoker | Low | Low | Low |
| Asymptomatic smoker | Elevated | 3 x Elevated | Low |
| Mild COPD (GOLD I) | Low | small elevation | Low |
| Moderate/Severe COPD (GOLD 2 & 3) | Elevated | Low | High |

Discussion

Estimated to become the third most common cause of death by 2020 (Murray and Lopez 1997), COPD is a major cause of morbidity and mortality worldwide. Forced expiratory volume in one second ($FEV_1$) is currently the most frequently used measurement of disease severity and progression, but does not correlate well with symptoms and other disease markers. There is currently much interest in the identification of suitable biomarkers that accurately reflect disease state and would thus prove useful as surrogates in diagnosis, monitoring of progression and as end points in clinical trials.

COPD is a complex, multi-factorial disease that activates both innate and acquired immune responses, the products of which are readily detected. This study focused on the identification of serum antibody responses to self-proteins either in native conformation or following modifications associated with oxidative stress, such as carbonylation and citrullination, that result in conformational changes which may render the protein immunogenic.

Carbonylation is the non-reversible, covalent modification of proteins or peptides (for example on cystein, histidine and/or lysine residues) by reactive carbonyls, such as those formed as a result of lipid peroxidation. Malondialdehyde (MDA), one of the endproducts of this peroxidation reaction is used as biomarker of oxidative stress (Rahman 2005; Chung and Adcock 2008). These carbonyl adducts such as these have been shown to be increased in the serum and tissues of smokers at higher levels than in non-smokers.

It was observed that elevated anti-vimentin antibody titres against both native and modified protein in COPD positive samples compared to samples from non-smokers were present. When antibody class responses to carbonylated vimentin were studied, increased IgG titres in more advanced COPD samples in the absence of elevated IgM responses were apparent. In contrast both IgM and IgG were elevated in asymptomatic smokers, while titres remained at base line in subjects with mild COPD. This would suggest that antibody class ratio may prove more useful than a single antibody measurement.

Since the initial report by Lee at al (Lee, Goswami et al. 2007) reporting anti-elastin autoimmunity in tobacco smoke induced emphysema, several reports have been published (Cottin, Fabien et al. 2009; Greene, Low et al. 2010; Brandsma, Kerstjens et al. 2011; Rinaldi, Lehouck et al. 2012) in which the authors have been unable to confirm a disease associated anti-elastin immune response. In light of this, we screened our cohort for antibodies to native and carbonylated elastin. We found no statistically significant difference in antibody titre between any of the groups to either the unmodified or carbonyl-modified antigen.

High levels of collagen remodelling in the lung are a hallmark of COPD, releasing peptide fragments that could be potentially immunogenic or serve directly as biomarkers. Indeed Leeming et al (Leeming, Sand et al. 2012) have recently reported significantly elevated levels of matrix metalloproteinase-degraded collagen types I, III, IV, V and VI in the serum of subjects with mild COPD compared to control subjects. Type IV collagen is the most abundant non-fibrillar collagen in the lung, present in the basement membrane (Konomi, Hayashi et al. 1984) and its expression and protein levels have been reported elevated in the lungs of patients with COPD (Kranenburg, Willems-Widyastuti et al. 2006). We did not observe any difference in serum antibody titre between COPD subjects, non-smoking controls or asymptomatic smokers. Other collagen proteins have also been screened and of them, collagen V, which is arousing interest as an autoantigen in several chronic diseases including respiratory diseases, has been shown to generate a T cell immunity that is more prevalent in smokers (Rinaldi, Lehouck et al. 2012).

Although we focused primarily on specific matrix proteins, we also investigated antibody responses to whole endothelial cells using a live cell ELISA. Sera from both COPD patients and asymptomatic smokers showed elevated levels of IgG compared to non-smokers. Although not statistically significant, IgM titre in the GOLD 3 group was reduced, such that when looking at IgM:IgG ratio, there was a significant reduction compared to non-smokers. While not significant, this was a trend echoed in the GOLD 2 and asymptomatic smoking group, suggesting an IgG driven response to cell surface endothelial proteins, driven by smoking or the COPD disease process.

As a blood-borne biomarker, antibodies are an attractive and convenient candidate as they can be obtained readily through a minimally invasive procedure, remaining stable in serum for extended periods of time. However there are limitations to their use. Antibodies are not a pre-requisite for autoimmune-type responses which may be driven only by T cells, and thus although we were unable to detect elevated antibody titres to some of the self-antigens we screened, it does not necessarily mean they have no role in disease pathogenesis or progression. Furthermore, antibody titres from an individual can vary widely over time. In the absence of stimulus the titre will decline, whereas following an exacerbatory episode in a subject with COPD, titres may be expected to increase. While our findings for carbonylated vimentin suggest a potential link between subclass ratio and disease state, this conclusion is taken from a small cohort and a single time point. It would be essential to expand the cohort and to perform analysis on serial samples taken over an extended period of time.

TABLE 1

Study subject details

|  | Age | M/F | Pack years | FEV/FVC | % pred $FEV_1$ |
|---|---|---|---|---|---|
| NS | 51 ± 2 | 8/5 | N/A | 0.98 ± 0.03 | 105 ± 4 |
| Smoker | 59 ± 2 | 14/8 | 28 ± 3 | 0.84 ± 0.03 | 86 ± 3 |
| GOLD 1 | 66 ± 2 | 1/4 | 56 ± 20 | 0.66 ± 0.01 | 88 ± 8 |
| GOLD 2 | 72 ± 2 | 10/2 | 43 ± 7 | 0.59 ± 0.02 | 62 ± 2 |
| GOLD 3 + 4 | 74 ± 2 | 6/4 | 34 ± 7 | 0.50 ± 0.03 | 40 ± 1 |

Data is depicted as Mean +/− SD. FEV1/FVC ratio is post bronchodilator for subjects with COPD but not smokers or non-smokers.
Abbreviations: pred = predicted; M = male; F = female; FEV1 = forced expiratory volume in 1 second; FVC = forced vital capacity.

REFERENCES

Bang, H., K. Egerer, et al. (2007). "Mutation and citrullination modifies vimentin to a novel autoantigen for rheumatoid arthritis." *Arthritis and rheumatism* 56(8): 2503-2511.

Brandsma, C. A., H. A. Kerstjens, et al. (2011). "The search for autoantibodies against elastin, collagen and decorin in COPD." *The European respiratory journal: official journal of the European Society for Clinical Respiratory Physiology* 37(5): 1289-1292.

Brusselle, G. G., T. Demoor, et al. (2009). "Lymphoid follicles in (very) severe COPD: beneficial or harmful?" *The European respiratory journal: official journal of the European Society for Clinical Respiratory Physiology* 34(1): 219-230.

Burcham et al. (2010) Intermediate Filament Carbonylation During Acute Acrolein Toxicity in A549 Lung Cells: Functional Consequences, Chaperone Redistribution, and PRotection by Bisulfite Cerami, C., H. Founds, et al. (1997). "Tobacco smoke is a source of toxic reactive glycation products." *Proceedings of the National Academy of Sciences of the United States of America* 94(25): 13915-13920.

Chung, K. F. and I. M. Adcock (2008). "Multifaceted mechanisms in COPD: inflammation, immunity, and tissue repair and destruction." *The European respiratory journal: official journal of the European Society for Clinical Respiratory Physiology* 31(6): 1334-1356.

Cottin, V., N. Fabien, et al. (2009). "Anti-elastin autoantibodies are not present in combined pulmonary fibrosis and emphysema." *The European respiratory journal: official journal of the European Society for Clinical Respiratory Physiology* 33(1): 219-221.

Feghali-Bostwick, C. A., A. S. Gadgil, et al. (2008). "Autoantibodies in patients with chronic obstructive pulmonary disease." *American journal of respiratory and critical care medicine* 177(2): 156-163.

Greene, C. M., T. B. Low, et al. (2010). "Anti-proline-glycine-proline or antielastin autoantibodies are not evident in chronic inflammatory lung disease." *American journal of respiratory and critical care medicine* 181(1): 31-35.

Haberland, M. E., A. M. Fogelman, et al. (1982). "Specificity of receptor-mediated recognition of malondialdehyde-modified low density lipoproteins." *Proceedings of the National Academy of Sciences of the United States of America* 79(6): 1712-1716.

Hogg, J. C., F. Chu, et al. (2004). "The nature of small-airway obstruction in chronic obstructive pulmonary disease." *The New England journal of medicine* 350(26): 2645-2653.

Kirkham, P. A., G. Caramori, et al. (2011). "Oxidative stress-induced antibodies to carbonyl-modified protein correlate with severity of chronic obstructive pulmonary disease." *American journal of respiratory and critical care medicine* 184(7): 796-802.

Konomi, H., T. Hayashi, et al. (1984). "Localization of type V collagen and type IV collagen in human cornea, lung, and skin. Immunohistochemical evidence by anti-collagen antibodies characterized by immunoelectroblotting." *The American journal of pathology* 116(3): 417-426.

Kranenburg, A. R., A. Willems-Widyastuti, et al. (2006). "Enhanced bronchial expression of extracellular matrix proteins in chronic obstructive pulmonary disease." *American journal of clinical pathology* 126(5): 725-735.

Kuo, Y. B., C. A. Chang, et al. (2010). "Identification and clinical association of anti-cytokeratin 18 autoantibody in COPD." *Immunology letters* 128(2): 131-136.

Lee, S. H., S. Goswami, et al. (2007). "Antielastin autoimmunity in tobacco smoking-induced emphysema." *Nature medicine* 13(5): 567-569.

Leeming, D. J., J. M. Sand, et al. (2012). "Serological investigation of the collagen degradation profile of patients with chronic obstructive pulmonary disease or idiopathic pulmonary fibrosis." *Biomarker insights* 7: 119-126.

Makrygiannakis, D., M. Hermansson, et al. (2008). "Smoking increases peptidylarginine deiminase 2 enzyme expression in human lungs and increases citrullination in BAL cells." *Annals of the rheumatic diseases* 67(10): 1488-1492.

Murray, C. J. and A. D. Lopez (1997). "Global mortality, disability, and the contribution of risk factors: Global Burden of Disease Study." *Lancet* 349(9063): 1436-1442.

Negre-Salvayre, A., C. Coatrieux, et al. (2008). "Advanced lipid peroxidation end products in oxidative damage to proteins. Potential role in diseases and therapeutic prospects for inhibitors." *British Journal of Pharmacology* 153(1): 6-20

Nicholl, I. D. and R. Bucala (1998). "Advanced glycation endproducts and cigarette smoking." *Cellular and molecular biology* 44(7): 1025-1033.

Nicholl, I. D., A. W. Stitt, et al. (1998). "Increased levels of advanced glycation endproducts in the lenses and blood vessels of cigarette smokers." *Molecular medicine* 4(9): 594-601.

Rahman, I. (2005). "Oxidative stress in pathogenesis of chronic obstructive pulmonary disease: cellular and molecular mechanisms." *Cell biochemistry and biophysics* 43(1): 167-188.

Rinaldi, M., A. Lehouck, et al. (2012). "Antielastin B-cell and T-cell immunity in patients with chronic obstructive pulmonary disease." *Thorax* 67(8): 694-700.

Saetta, M., A. Di Stefano, et al. (1998). "CD8+ T-lymphocytes in peripheral airways of smokers with chronic obstructive pulmonary disease." *American journal of respiratory and critical care medicine* 157(3 Pt 1): 822-826.

Sullivan, A. K., P. L. Simonian, et al. (2005). "Oligoclonal CD4+ T cells in the lungs of patients with severe emphysema." *American journal of respiratory and critical care medicine* 172(5): 590-596.

Talhout, R., T. Schulz, et al. (2011). "Hazardous compounds in tobacco smoke." *International journal of environmental research and public health* 8(2): 613-628.

van der Strate, B. W., D. S. Postma, et al. (2006). "Cigarette smoke-induced emphysema: A role for the B cell?" *American journal of respiratory and critical care medicine* 173(7): 751-758.

Varani, K., G. Caramori, et al. (2006). "Alteration of adenosine receptors in patients with chronic obstructive pulmonary disease." *American journal of respiratory and critical care medicine* 173(4): 398-406.

Waalkens, H. J., P. J. Merkus, et al. (1993). "Assessment of bronchodilator response in children with asthma. Dutch CNSLD Study Group." *Eur Respir J* 6(5): 645-651.

Example 2

Activated Complement Deposition in COPD Lungs and Complement-Mediated Endothelial Cell Death AutoAntibodies/complement triggered endothelial cell death in GOLD3 COPD:

Coat 4×96 well plates with 25 µl/well 1% gelatine and incubate 30 mins 37° C.

Remove gelatine and seed with 1×104 HUVEC/well in Med 199 with 5% FCS. Incubate o/n 37° C.

Remove medium and replace with 50 µl/well Med 199 with 5% test serum. Test each sample in triplicate. Incubate 1 h 37° C.

Remove medium and replace with 100 µl 5% normal serum or heat inactivated normal serum in Med199. Incubate 1 h 37° C.

Measure cytotoxicity/survival by MTS. Add 20 µl/well MTS reagent and incubate 2 h at 37° C. Read plates at 490 nm.

The amount of cell death per well is expressed as a percentage relative to untreated control cells. For each patient test sample, the % of cell death attributed to Ab-mediated activated compliment is then calculated by subtracting the amount of cell death in wells treated with heat inactivated serum from wells incubated with untreated serum.

For healthy control subjects there was no statistically significant difference in cell death between heat inactivated and untreated serum. In contrast the % cell death between heat inactivated and untreated serum with Ab from GOLD3 COPD patients was significant (p<0.01) as determined by matched pair student T-test.

Example 3

Assay Formats Suitable for Compound Screening

[Suitable assays or protocols for assessing compounds, for example anti-idiotypic antibodies/antibody fragments, will be well known to those skilled in the art in view of the teaching herein. As an example, one could perform tests in a completion based immunoassay format, whereby the anti-idiotype or compound would be incubated with the serum sample first before adding to the immunoassay plate where the carbonylated antigen is immobilised. Alternatively, the anti-idiotype or compound may be added to the plate with the antigen first before the serum sample is added. A high throughput format may be used Example 4

Treatment Protocols

A potential scenario would be as follows:

The IgG/IgM ratio would be assessed at the first visit to the GP/clinician and then yearly thereafter (or more frequently if subjected to repeated exacerbatory episodes) until the IgG/IgM ratio starts to rise. Treatment regimes may then be started and the IgG/IgM ratio monitored as frequently as necessary, such as monthly. Monitoring will continue, such as monthly, until the IgG/IgM ratio falls, then gradually monitoring less frequently until once or twice a year.

Example 5

Oxidative Stress in COPD

The following review is expected to be published in the journal Chest in July 2013 (Kirkham and Barnes).

Abstract

Oxidative stress is now recognized as being a major predisposing factor in the pathogenesis of COPD. Existing therapies for COPD are ineffective at halting disease progression, with bronchodilators being the mainstay of pharmacotherapy, providing symptomatic relief only. It is therefore important for a better understanding of the underlying mechanisms by which oxidative stress drives disease pathogenesis, in order to develop novel and more effective therapies. Anti-oxidant capacity in COPD is substantially reduced as a result of cigarette smoking and exacerbations, with oxidative stress persisting long after the cessation of cigarette smoking or exacerbation, due to the continued production of reactive oxygen species (ROS) from endogenous sources. We discuss how oxidative stress arises in the lung, how it is neutralized, what genetic factors may predispose to the development of COPD and how this impacts on inflammation and autoimmunity, and development of emphysema and small airway disease. Finally, various strategies have been considered to neutralize the increased oxidative burden present in COPD. This review highlights why current anti-oxidant strategies have so far failed and what promising alternatives are on the horizon. Moreover, a number of studies have shown that there is no single "magic bullet" to combat oxidative stress, but instead a combination therapy, targeting oxidative stress in the various sub-cellular compartments, may prove to be more effective in COPD.

Key words: reactive oxygen species, antioxidants, inflammation, NF-κB, Nrf2, autoantibody

ABBREVIATIONS $FEV_1$ forced expiratory volume in 1 second
GSH reduced glutathione
GST glutathione-S-transferase
$H_2O_2$ hydrogen peroxide
HDAC histone deacetylase
4HNE 4-hydroxy-2-nonenal
IL interleukin
MDA malondialdehyde NF-κB nuclear factor-κB
NOX NADPH oxidase
Nrf2 nuclear erythroid-2 related factor 2
ROS reactive oxygen species
SOD superoxide dismutase
TGF transforming growth factor Introduction Chronic obstructive pulmonary disease (COPD) is a major and increasing global health problem, which is set to become the third leading cause of death worldwide by 2020. It currently affects around 10% of the population over 45 years but this rises to 50% in heavy smokers[1]. The major etiological factor driving this disease is likely to be oxidative and carbonyl stress in the lungs following long-term exposure to cigarette smoke or the combustion products of biomass fuels[2]. Oxidative stress arises as a result of endogenous anti-oxidant defenses being genetically impaired and/or overwhelmed by the presence of reactive oxygen species (ROS). This in turn can lead to carbonyl stress where oxidative damage to the surrounding tissues leads to the formation of highly reactive organic molecules that can modify proteins non-enzymatically. COPD is characterized by chronic inflammation and remodeling of the small airways and destruction of the lung parenchyma (emphysema)[3]. A striking feature of COPD is its failure to resolve when exposure to cigarette smoke has stopped,[4] which has led to the suggestion that other endogenous factors, such as autoimmunity or persistent infection may also be driving the disease.[1,5]

Persistent Lung and Systemic Oxidative Stress in COPD

There is evidence for oxidative and carbonyl stress in COPD, particularly during acute exacerbations. Alveolar macrophages from COPD patients are more activated and release increased amounts of reactive oxygen species (ROS) in the form of the superoxide radical and hydrogen peroxide ($H_2O_2$)[6]. Similarly, activated peripheral blood neutrophils from COPD patients release increased amounts of ROS, particularly during exacerbations. Markers of oxidative stress and carbonyl stress in COPD include elevated concentrations of nitro-tyrosine[7] and lipid peroxidation products, such as 8-isoprostane, 4-hydroxy-2-nonenal (4HNE) and malondialdehyde (MDA)[8;9]. In contrast, concentrations of the endogenous anti-oxidant glutathione are lower in BAL fluid from COPD patients with frequent exacerbations compared to those with stable COPD[10]. Although more refined non-invasive methods of assessing oxidative stress have been developed they are limited due to a lack of standardization[11].

Despite this, several markers of oxidative stress, for example $H_2O_2$, carbon monoxide, myeloperoxidase (MPO)[12,11] and markers of oxidative tissue damage such as 8-isoprostane[13], and carbonyl stress in the form of MDA[14], have consistently been shown to be elevated in exhaled breath or exhaled breath condensate from COPD patients. Moreover, systemic exposure to oxidative stress in COPD is also indicated by increased carbonyl adducts, such as 4-hydroxynonenal in respiratory[8] and skeletal muscle[15].

Source of ROS in the Lung

The lung is particularly vulnerable to injury from environmental oxidative stress due in part to its anatomical structure. It is constantly exposed to sources of endogenous oxidative stress generated by mitochondrial respiration and inflammatory responses to bacterial and viral infections within the lung. The environmental sources of airborne oxidative stress include oxidant gases and ultrafine particulate material and nanoparticles from industrial pollution and car exhaust fumes. However, the single most important etiological factor in causing COPD in the Western world is cigarette smoking, with inhalation of combustion products from enclosed cooking fires being an important additional etiological factor in developing countries[16].

Whilst exposure to cigarette smoke can drive the onset of COPD, once the disease has become established cessation of smoking does not stop the continued presence of oxidative stress and progression of disease[17]. The continued presence of oxidative stress most likely arises from endogenous sources such as mitochondrial respiration. Indeed, airway epithelial cells when exposed to carbonyl stress induce the production of mitochondria-derived R[18] and airway smooth muscle cells from COPD patients produce greater amounts of mitochondrial-derived ROS when subject to inflammatory stress from IL-1, TNF□ and IFN□. Pathway analysis has identified mitochondrial dysfunction around complexes I and III as being tightly associated with COPD[19]. In addition, other sources of intracellular ROS include the cytoplasmic ROS generating enzymes, such as NADPH oxidase (NOX) and the xanthine/xanthine oxidase system as well as the heme peroxidases, levels of which are elevated in broncholavage fluid and inflammatory cells within the airways of COPD patients[20;21].

The abundantly produced superoxide radical is a relatively weak oxidizing agent but is the precursor for other more damaging ROS species (FIG. 1), such as the hydroxyl radical which is elevated in COPD[22], or the very powerful and damaging peroxynitrite radical formed by the rapid reaction of superoxide with nitric oxide[23]. Similarly MPO, released from activated neutrophils which accumulate in the lungs of COPD patients, produces very destructive hypochlorous acid. However, in healthy cells intracellular anti-oxidant defenses are able to efficiently mop up these ROS species, thus limiting their impact.

Carbonyl Stress in COPD

ROS generation has been directly linked to oxidation of proteins, lipids, carbohydrates and DNA. The major outcome is the formation of reactive carbonyls and their reaction with proteins, otherwise known as protein carbonylation. This accumulation of reactive carbonyls and subsequent protein carbonylation has been commonly referred to as 'carbonyl stress'. It is predominantly associated with chronic disease[24] and aging. Unlike other post-translational modifications, protein carbonylation is non-enzymatic and targets specific peptide residues, such as lysine, arginine, cysteine and histidine.

Protein carbonylation is increasingly recognized as a major driver of the underlying pathology associated with many chronic diseases[25]. It is present in both smokers and COPD patients[26]. Increased levels of free carbonyls, such as MDA, a major product of lipid peroxidation, have also been detected in the lungs of COPD patients[9]. Levels of carbonyl stress are correlated with disease severity as measured by the decline in forced expiratory volume in 1 second $(FEV_1)$[8]. Like many post-translational protein modifications, protein carbonylation can modify protein function, disrupting normal cell function and physiological mechanisms[27].

Antioxidant Defenses in the Lung

Because the lung is constantly exposed to both external and endogenous sources of oxidative stress, it has evolved a number of efficient anti-oxidant defensive strategies, of which glutathione (GSH) plays an important part. Moreover, up to 20% of all glutathione produced is found within the mitochondria in order to neutralize endogenous ROS production as a by-product of metabolism[28]. Protecting the exposed surface of the lung from the environment is the epithelial lining fluid, which contains several antioxidants that include ascorbic acid (vitamin C), α-tocopherol (vitamin E) and uric acid. Larger molecules such as, albumin and mucin, can also act as sacrificial anti-oxidants due to the presence of exposed sulphydryl groups. Several studies have shown a clear association between reduced levels of the antioxidants in the lung, such as α-tocopherol and ascorbic acid, and deteriorating pulmonary function in COPD. This however, may simply reflect an increased oxidative burden as a result of repeated exacerbations. No studies to date have shown that dietary supplementation with anti-oxidants leads to clinical improvement[29]. However, a 10 year follow-up study did find that anti-oxidant supplementation reduced the risk of developing chronic lung disease by 10%[30] and lowered carbonyl stress levels in the lung[31].

The exposure of airway epithelial cells from healthy subjects to acute oxidative stress triggers increased GSH synthesis, by up-regulating the expression and activity of a key enzyme in GSH synthesis, glutamylcysteine ligase[32]. However, the amount of this enzyme is lowered around the central bronchial epithelium and in alveolar macrophages from smokers and patients with COPD[33], suggesting a defective regulatory mechanism. Similar differential responses between COPD and control subjects were apparent with other GSH-dependent anti-oxidant enzymes, glutathione-S-transferase pi isoenzyme (GSTpi), glutathione-S-transferase M1 (GSTM1) and glutathione peroxidase.[34] A genetic deletion mutation in GSTM1 is associated with the development of emphysema in smokers and increased susceptibility to developing COPD[35]. Similarly, genetic polymorphisms in the GSTpi have been associated with COPD[36].

Transforming growth factor (TGF)-β expression is increased in COPD and inhibits the expression of the antioxidant enzymes catalase and superoxide dismutase (SOD)2, also known as Mn-SOD, in airway smooth muscle cells[37]. Both these enzymes, which are critical for neutralizing mitochondrial derived ROS, are under the control of the transcription factor FOXO3. Moreover, a deficiency in FOXO3 activity has previously been associated with COPD[38]. Gene polymorphisms for SOD2 have also been shown to be highly associated with COPD[39], although few data are available to show how these polymorphisms equate to changes in functional activity. Similarly, polymorphisms in SOD3 (extracellular SOD) have also been linked to both reduced lung function in COPD[49] and protection against the development of COPD in smokers when SOD3 activity is enhanced[41]. Over 200 cellular anti-oxidant and detoxification enzymes are under the control of the transcription factor nuclear erythroid-2 related factor 2 (Nrf2), which regulates gene expression through binding to anti-oxidant response elements (ARE) within the promoters of the many antioxidant and cytoprotective genes[42]. COPD patients have reduced expression of Nrf2 responsive genes due to reduced Nrf2 activity[43]. Up-regulation or restoration of Nrf2 activity may, therefore, prove to be of therapeutic benefit in COPD[44].

Oxidative Stress and Inflammation in the Airways

At least 50 different cytokines and chemokines have been found to be associated with COPD. Many of the intracellular signaling pathways triggered and/or driving the release of these inflammatory mediators are sensitive to oxidative stress as they incorporate redox-sensitive molecular targets, such as the transcription factor nuclear factor-κB (NF-κB) and signaling molecules such as Ras/Rac, Jun-N-terminal kinase (JNK), p38 mitogen-activated protein kinase (MAPK) and protein tyrosine phosphatases. Oxidative stress can activate the NF-κB pathway at many levels and NF-κB expression and activation is increased in COPD and correlates with airflow limitation[45]. Moreover, ROS also act as intracellular second messengers, as inflammatory stimuli induce micro-oxidative bursts which are essential for cellular activation[46]. Carbonyl stress in the form of electrophilic carbonyls can also impact on many different signaling pathways[47]. As with oxidative stress, this is propagated through the targeting of critical cysteine residues in susceptible signaling molecules[47].

Resolution of the inflammatory response is equally as important as its induction and the clearance of apoptotic cells by phagocytosis plays a major role in this process. Phagocytosis is impaired in COPD[48] and a failure to remove apoptotic cells can lead to secondary necrosis and continued inflammation in COPD[49]. The impact of oxidative/carbonyl stress on phagocytosis would appear multi-factorial with the effects being both intra- and extracellular. Intracellularly, oxidative stress activates RhoA impairing phagocytosis through changes in cytoskeletal reorganization[50]. Extracellularly, oxidative/carbonyl stress results in carbonylation of tissue proteins creating competition for the same pattern recognition receptors (PRRs) expressed on alveolar macrophages that recognize and clear both carbonyl-modified protein and apoptotic cells[51]. More recently, these PRRs necessary for phagocytosis have themselves been shown to be carbonyl modified and thereby impaired[52]. The ability of corticosteroids to repress pro-inflammatory gene expression is also impaired in COPD as a result of oxidative stress[53]. Carbonylation and nitration reduce the activity and expression of an important transcriptional co-repressor histone deacetylase (HDAC)2 which is essential for the suppression of activated inflammatory genes and the anti-inflammatory actions of corticosteroids.[54,55] Moreover loss of HDAC2 activity, as observed in COPD[56], has also been demonstrated to lead to a loss of Nrf-2 activity through increased Nrf-2 acetylation thereby decreasing Nrf-2 stability and expression[43]. This leads to an interesting paradox whereby oxidative/carbonyl stress will activate Nrf-2 inducing the expression of protective anti-oxidant defenses, but chronic exposure to oxidative/carbonyl stress can inhibit/reduce the effectiveness of Nrf-2 activation by reducing HDAC2 activity. Indeed, oxidative stress activates the enzyme phosphoinositide-3-kinase-δ, which is also responsible for reducing HDAC2 activity and expression[57]. Another transcriptional co-repressor sirtuin-1 is similarly impacted by oxidative stress, reducing both its expression and activity leading to an accelerated aging process[58] and the increased likelihood of developing emphysema as the lung ages more rapidly[59]. Oxidative stress can thus result in enhanced inflammatory gene expression, failure to resolve the inflammatory response, corticosteroid insensitivity, a decreased capacity to induce endogenous antioxidant defences and a rapidly aging lung in COPD with increased risk of developing emphysema.

Oxidative Stress and Autoimmunity in COPD

Accumulating evidence has shown that there is an autoimmune component in COPD[60]. Until recently, a mechanistic link between exposure to oxidative stress and developing autoimmunity in COPD was not established. However, autoantibodies against carbonyl-modified self proteins as a result of oxidative stress, are elevated in COPD serum, and increase with disease severity. Since these autoantibodies are complement fixing they could contribute to parenchymal lung destruction[26]. Carbonyl-modified proteins are highly immunogenic and can result in autoimmunity[61]. Carbonyl-modified proteins are recognized by the innate immune system through pattern recognition receptors that are expressed on antigen-presenting cells, such as macrophages and dendritic cells,[62,63] whereupon these potent immunogens are processed and re-expressed in association with MHCII, thereby facilitating the activation of an acquired immune response. Indeed, COPD patients exhibit a strong type 1 immune response in the lower airways with the pulmonary accumulation of Th1 cells[1] and dendritic cells in the small airways of COPD patients[64], expressing increased amounts of MHCII. It is not clear however, whether this autoantibody response to oxidatively-modified protein epitopes in COPD is destructive, protective or simply a bystander effect. However, the auto-antibodies against carbonyl-modified protein were of a potentially destructive IgG1 isotype[26] and evidence of corresponding immunoglobulin (IgG) and complement (C3) deposition have been observed in COPD[26,65].

Besides oxidative stress creating the essential neo-antigens, it also helps to drive the influx of immune cells necessary to recognize and process these neo-antigens. Increased oxidative stress in the lungs causes the release of CCL20 and CCL2 which in turn triggers the recruitment of dendritic cells, monocytes and lymphocytes. Helping to orchestrate this immune response in COPD are elevated levels of interleukin (IL)-17 and IL-18[66,67] which are important for the activation and maturation of B cells and promoting an autoimmune response. IL-18 promotes IL-17 expression and oxidative stress has been demonstrated to activate IL-18 signaling pathways with attenuation of IL-18 preventing further lung destruction[68].

Therapeutic Implications

There are currently no treatments that reverse or even slow the progression of CORD. Inhaled corticosteroids are highly effective in reducing the inflammatory component in asthma, but provide little therapeutic benefit in COPD. Whilst they may have a small effect in reducing exacerbation frequency, they fail to reduce the inflammatory component and halt the inexorable decline in lung function. This resistance can be attributed to cigarette smoke or oxidative stress[69]. Targeting oxidative/carbonyl stress with pharmacological antioxidants or boosting the endogenous levels of antioxidants may therefore prove to be beneficial in the treatment and management of COPD. To date however, no clinical studies have shown that antioxidant treatment alone is beneficial or able to lead to the restoration in corticosteroid function. However, compounds such as theophylline have shown a clinically significant effect in enhancing corticosteroid efficacy in COPD patients[70]. Interestingly, the target binding profile of theophylline is redox-sensitive and is greater under conditions of oxidative stress, which may account for its efficacy in enhancing steroid efficacy in COPD[71].

The largest trial of an antioxidant in COPD was the BRONCUS study which failed to show any overall effect of oral N-acetyl cysteine on slowing disease progression, or exacerbation frequency, although there was apparent benefit in the patients not treated with inhaled corticosteroids[72]. An earlier clinical study (Equalife) using a different anti-oxidant (erdosteine) showed similar findings[73]. The failure of these clinical studies may be attributable to several reasons; the failure of the antioxidant to be targeted to the correct cellular sub compartment where the anti-oxidant is needed most, the potency of the antioxidant, the dosage and frequency used in the clinical trials may not have been high enough. Consequently, the development of novel wide-spectrum small molecule antioxidants with good bioavailability and potency are needed for clinical use in COPD. A number of alternative antioxidant strategies (reviewed elsewhere) have been proposed, some of which have shown promise. Perhaps the most encouraging approaches to anti-oxidant therapy lie with the use of new Nrf-2 activators which are significantly more potent than sulforophane[75] and may also prevent oxidative stress-induced autoimmunity[76]. The Nrf-2 activator BG-12 recently successfully completed phase III trials for use in multiple sclerosis and is now awaiting approval. However another Nrf-2 activator bardoxolone methyl (CDDO) failed to complete phase III due to an excess of serious adverse events. Although both drugs are covalent activators of Nrf-2, they differ in the profile of Nrf-2 inducible genes that are activated, are structurally different and consequently may have different off-target binding profiles to account for the different clinical outcomes. Other promising approaches include the SOD mimetics, such as AEOL10113, NOX inhibitors such as celestrol[77] and myeloperoxidase inhibitors, such as 2-thioxanthine and ADZ5904[78].

Conclusions

Elevated levels of ROS and carbonyls are found in COPD and these may be associated with increased inflammation, airway remodeling, autoimmunity and corticosteroid resistance. In addition systemic oxidative stress may also be a causal link in many COPD co-morbidities such as cardiovascular diseases and metabolic syndrome. Local oxidative stress may also promote the development of lung cancer. Following the initial environmental exposure to ROS, the subsequent intracellular sources and chronicity of oxidative stress may be important to understanding the pathophysiology of this disease. The failure of existing anti-oxidants in COPD studies indicates the need to develop novel more potent anti-oxidants targeted to the correct intracellular compartment. Combinations of antioxidants, targeting different cellular compartments, may prove more effective than monotherapy. In a similar manner, combining antioxidants with anti-inflammatory drugs, bronchodilators, antibiotics, and statins may complement, or in the case of corticosteroids, improve/restore their efficacy.

REFERENCES

Reference List (1) Cosio M G, Saetta M, Agusti A. Immunologic aspects of chronic obstructive pulmonary disease. N Engl J Med 2009; 360(23):2445-2454.
(2) Salvi S, Barnes P J. Is exposure to biomass smoke the biggest risk factor for COPD globally? Chest 2010; 138(1):3-6.
(3) Hogg J C, Chu F, Utokaparch S et al. The nature of small-airway obstruction in chronic obstructive pulmonary disease. N Engl J Med 2004; 350(26):2645-2653.
(4) Hogg J C. Why does airway inflammation persist after the smoking stops? Thorax 2006; 61(2):96-97.
(5) Taraseviciene-Stewart L, Douglas I S, Nana-Sinkam P S et al. Is alveolar destruction and emphysema in chronic obstructive pulmonary disease an immune disease? Proc Am Thorac Soc 2006; 3(8):687-690.
(6) Schaberg T, Klein U, Rau M et al. Subpopulations of alveolar macrophages in smokers and nonsmokers: relation to the expression of CD11/CD18 molecules and superoxide anion production. Am J Respir Crit Care Med 1995; 151(5):1551-1558.
(7) Ichinose M, Sugiura H, Yamagata S et al. Increase in reactive nitrogen species production in chronic obstructive pulmonary disease airways. Am J Respir Crit Care Med 2000; 162(2 Pt 1):701-706.

(8) Rahman I, van Schadewijk A A, Crowther A J et al. 4-Hydroxy-2-nonenal, a specific lipid peroxidation product, is elevated in lungs of patients with chronic obstructive pulmonary disease. Am J Respir Crit Care Med 2002; 166(4):490-495.

(9) Kluchova Z, Petrasova D, Joppa P et al. The association between oxidative stress and obstructive lung impairment in patients with COPD. Physiol Res 2007; 56(1):51-56.

(10) Drost E M, Skwarski K M, Sauleda J et al. Oxidative stress and airway inflammation in severe exacerbations of COPD. Thorax 2005; 60(4):293-300.

(11) Montuschi P. Exhaled breath condensate analysis in patients with COPD. Clin Chim Acta 2005; 356(1-2):22-34.

(12) Paredi P, Kharitonov S A, Barnes P J. Analysis of expired air for oxidation products. Am J Respir Crit Care Med 2002; 166(12 Pt 2):S31-S37.

(13) Paredi P, Kharitonov S A, Leak D et al. Exhaled ethane, a marker of lipid peroxidation, is elevated in chronic obstructive pulmonary disease. Am J Respir Crit Care Med 2000; 162(2 Pt 1):369-373.

(14) Bartoli M L, Novelli F, Costa F et al. Malondialdehyde in exhaled breath condensate as a marker of oxidative stress in different pulmonary diseases. Mediators Inflamm 2011; 2011:891752.

(15) Barreiro E, Peinado V I, Galdiz J B et al. Cigarette smoke-induced oxidative stress: A role in chronic obstructive pulmonary disease skeletal muscle dysfunction. Am J Respir Crit Care Med 2010; 182(4):477-488.

(16) Kodgule R, Salvi S. Exposure to biomass smoke as a cause for airway disease in women and children. Curr Opin Allergy Clin Immunol 2012; 12(1):82-90.

(17) Louhelainen N, Rytila P, Haahtela T et al. Persistence of oxidant and protease burden in the airways after smoking cessation. BMC Pulm Med 2009; 9:25.

(18) van der Toorn M, Rezayat D, Kauffman H F et al. Lipid-soluble components in cigarette smoke induce mitochondrial production of reactive oxygen species in lung epithelial cells. Am J Physiol Lung Cell Mol Physiol 2009; 297(1):L109-L114.

(19) Aguilera-Aguirre L, Bacsi A, Saavedra-Molina A et al. Mitochondrial dysfunction increases allergic airway inflammation. J Immunol 2009; 183(8):5379-5387.

(20) Pinamonti S, Leis M, Barbieri A et al. Detection of xanthine oxidase activity products by EPR and HPLC in bronchoalveolar lavage fluid from patients with chronic obstructive pulmonary disease. Free Radic Biol Med 1998; 25(7):771-779.

(21) Aaron S D, Angel J B, Lunau M et al. Granulocyte inflammatory markers and airway infection during acute exacerbation of chronic obstructive pulmonary disease. Am J Respir Crit Care Med 2001; 163(2):349-355.

(22) Ghio A J, Pritchard R J, Dittrich K L et al. Non-heme (Fe3+) in the lung increases with age in both humans and rats. J Lab Clin Med 1997; 129(1):53-61.

(23) Janssen-Heininger Y M, Persinger R L, Korn S H et al. Reactive nitrogen species and cell signaling: implications for death or survival of lung epithelium. Am J Respir Crit Care Med 2002; 166(12 Pt 2):S9-S16.

(24) Dalle-Donne I, Giustarini D, Colombo R et al. Protein carbonylation in human diseases. Trends Mol Med 2003; 9(4):169-176.

(25) Negre-Salvayre A, Coatrieux C, Ingueneau C et al. Advanced lipid peroxidation end products in oxidative damage to proteins. Potential role in diseases and therapeutic prospects for the inhibitors. Br J Pharmacol 2008; 153(1):6-20.

(26) Kirkham P A, Caramori G, Casolari P et al. Oxidative stress-induced antibodies to carbonyl-modified protein correlate with severity of chronic obstructive pulmonary disease. Am J Respir Crit Care Med 2011; 184(7):796-802.

(27) Kirkham P. Oxidative stress and macrophage function: a failure to resolve the inflammatory response. Biochem Soc Trans 2007; 35(Pt 2):284-287.

(28) Rahman I, Biswas S K, Jimenez L A et al. Glutathione, stress responses, and redox signaling in lung inflammation. Antioxid Redox Signal 2005; 7(1-2):42-59.

(29) Tsiligianni I G, van der Molen T. A systematic review of the role of vitamin insufficiencies and supplementation in COPD. Respir Res 2010; 11:171.

(30) Agler A H, Kurth T, Gaziano J M et al. Randomised vitamin E supplementation and risk of chronic lung disease in the Women's Health Study. Thorax 2011; 66(4):320-325.

(31) de B J, Barreiro E, Romieu I et al. Dietary modulation of oxidative stress in chronic obstructive pulmonary disease patients. Free Radic Res 2010; 44(11):1296-1303.

(32) Shi M M, Iwamoto T, Forman H J. gamma-Glutamylcysteine synthetase and GSH increase in quinone-induced oxidative stress in BPAEC. Am J Physiol 1994; 267(4 Pt 1):L414-L421.

(33) Harju T, Kaarteenaho-Wiik R, Soini Y et al. Diminished immunoreactivity of gamma-glutamylcysteine synthetase in the airways of smokers' lung. Am J Respir Crit Care Med 2002; 166(5):754-759.

(34) Tomaki M, Sugiura H, Koarai A et al. Decreased expression of antioxidant enzymes and increased expression of chemokines in COPD lung. Pulm Pharmacol Ther 2007; 20(5):596-605.

(35) Cheng S L, Yu C J, Chen C J et al. Genetic polymorphism of epoxide hydrolase and glutathione S-transferase in COPD. Eur Respir J 2004; 23(6):818-824.

(36) DeMeo D L, Hersh C P, Hoffman E A et al. Genetic determinants of emphysema distribution in the national emphysema treatment trial. Am J Respir Crit Care Med 2007; 176(1):42-48.

(37) Michaeloudes C, Sukkar M B, Khorasani N M et al. TGF-beta regulates Nox4, MnSOD and catalase expression, and IL-6 release in airway smooth muscle cells. Am J Physiol Lung Cell Mol Physiol 2011; 300(2):L295-L304.

(38) Hwang J W, Rajendrasozhan S, Yao H et al. FOXO3 deficiency leads to increased susceptibility to cigarette smoke-induced inflammation, airspace enlargement, and chronic obstructive pulmonary disease. J Immunol 2011; 187(2):987-998.

(39) Pietras T, Szemraj J, Witusik A et al. The sequence polymorphism of MnSOD gene in subjects with respiratory insufficiency in COPD. Med Sci Monit 2010; 16(9): CR427-CR432.

(40) Dahl M, Bowler R P, Juul K et al. Superoxide dismutase 3 polymorphism associated with reduced lung function in two large populations. Am J Respir Crit Care Med 2008; 178(9):906-912.

(41) Young R P, Hopkins R, Black P N et al. Functional variants of antioxidant genes in smokers with COPD and in those with normal lung function. Thorax 2006; 61(5): 394-399.

(42) Kobayashi M, Yamamoto M. Nrf2-Keap1 regulation of cellular defense mechanisms against electrophiles and reactive oxygen species. Adv Enzyme Regul 2006; 46:113-140.

(43) Mercado N, Thimmulappa R, Thomas C M et al. Decreased histone deacetylase 2 impairs Nrf2 activation by oxidative stress. Biochem Biophys Res Commun 2011; 406(2):292-298.

(44) Barnes P J. Defective antioxidant gene regulation in COPD: a case for broccoli. Am J Respir Crit Care Med 2008; 178(6):552-554.

(45) Di Stefano A., Caramori G, Oates T et al. Increased expression of nuclear factor-kappaB in bronchial biopsies from smokers and patients with COPD. Eur Respir J 2002; 20(3):556-563.

(46) Park H S, Kim S R, Lee Y C. Impact of oxidative stress on lung diseases. Respirology 2009; 14(1):27-38.

(47) Groeger A L, Freeman B A. Signaling actions of electrophiles: anti-inflammatory therapeutic candidates. Mol Intery 2010; 10(1):39-50.

(48) Donnelly L E, Barnes P J. Defective phagocytosis in airways disease. Chest 2012; 141(4):1055-1062.

(49) Vandivier R W, Henson P M, Douglas I S. Burying the dead: the impact of failed apoptotic cell removal (efferocytosis) on chronic inflammatory lung disease. Chest 2006; 129(6):1673-1682.

(50) Richens T R, Linderman D J, Horstmann S A et al. Cigarette smoke impairs clearance of apoptotic cells through oxidant-dependent activation of RhoA. Am J Respir Grit Care Med 2009; 179(11):1011-1021.

(51) Kirkham P A, Spooner G, Rahman I et al. Macrophage phagocytosis of apoptotic neutrophils is compromised by matrix proteins modified by cigarette smoke and lipid peroxidation products. Biochem Biophys Res Commun 2004; 318(1):32-37.

(52) Bozinovski S, Vlahos R, Zhang Y et al. Carbonylation caused by cigarette smoke extract is associated with defective macrophage immunity. Am J Respir Cell Mol Biol 2011; 45(2):229-236.

(53) Barnes P J, Adcock I M, Ito K. Histone acetylation and deacetylation: importance in inflammatory lung diseases. Eur Respir J 2005; 25(3):552-563.

(54) Meja K K, Rajendrasozhan S, Adenuga D et al. Curcumin restores corticosteroid function in monocytes exposed to oxidants by maintaining HDAC2. Am J Respir Cell Mol Biol 2008; 39(3):312-323.

(55) Ito K, Hanazawa T, Tomita K et al. Oxidative stress reduces histone deacetylase 2 activity and enhances IL-8 gene expression: role of tyrosine nitration. Biochem Biophys Res Commun 2004; 315(1):240-245.

(56) Ito K, Ito M, Elliott W M et al. Decreased histone deacetylase activity in chronic obstructive pulmonary disease. N Engl J Med 2005; 352(19):1967-1976.

(57) To Y, Ito K, Kizawa Y et al. Targeting phosphoinositide-3-kinase-delta with theophylline reverses corticosteroid insensitivity in chronic obstructive pulmonary disease. Am J Respir Crit Care Med 2010; 182(7):897-904.

(58) Nakamaru Y, Vuppusetty C, Wada H et al. A protein deacetylase SIRT1 is a negative regulator of metalloproteinase-9. FASEB J 2009; 23(9):2810-2819.

(59) Ito K, Barnes P J. COPD as a disease of accelerated lung aging. Chest 2009; 135(1):173-180.

(60) Kheradmand F, Shan M, Xu C et al. Autoimmunity in chronic obstructive pulmonary disease: clinical and experimental evidence. Expert Rev Clin Immunol 2012; 8(3):285-292.

(61) Kurien B T, Scofield R H. Autoimmunity and oxidatively modified autoantigens. Autoimmun Rev 2008; 7(7):567-573.

(62) Kirkham P A, Spooner G, Ffoulkes-Jones C et al. Cigarette smoke triggers macrophage adhesion and activation: role of lipid peroxidation products and scavenger receptor. Free Radic Biol Med 2003; 35(7):697-710.

(63) Allison M E, Fearon D T. Enhanced immunogenicity of aldehyde-bearing antigens: a possible link between innate and adaptive immunity. Eur J Immunol 2000; 30(10):2881-2887.

(64) Demedts I K, Bracke K R, Van P G et al. Accumulation of dendritic cells and increased CCL20 levels in the airways of patients with chronic obstructive pulmonary disease. Am J Respir Crit Care Med 2007; 175(10):998-1005.

(65) Feghali-Bostwick C A, Gadgil A S, Otterbein L E et al. Autoantibodies in patients with chronic obstructive pulmonary disease. Am J Respir Crit Care Med 2008; 177 (2):156-163.

(66) Di Stefano A., Caramori G, Gnemmi I et al. T helper type 17-related cytokine expression is increased in the bronchial mucosa of stable chronic obstructive pulmonary disease patients. Clin Exp Immunol 2009; 157(2):316-324.

(67) Imaoka H, Hoshino T, Takei S et al. Interleukin-18 production and pulmonary function in COPD. Eur Respir J 2008; 31(2):287-297.

(68) Kang M J, Homer R J, Gallo A et al. IL-18 is induced and IL-18 receptor alpha plays a critical role in the pathogenesis of cigarette smoke-induced pulmonary emphysema and inflammation. J Immunol 2007; 178(3):1948-1959.

(69) Culpitt S V, Rogers D F, Shah P et al. Impaired inhibition by dexamethasone of cytokine release by alveolar macrophages from patients with chronic obstructive pulmonary disease. Am J Respir Crit Care Med 2003; 167(1):24-31.

(70) Ford P A, Durham A L, Russell R E et al. Treatment effects of low-dose theophylline combined with an inhaled corticosteroid in COPD. Chest 2010; 137(6):1338-1344.

(71) Marwick J A, Wallis G, Meja K et al. Oxidative stress modulates theophylline effects on steroid responsiveness. Biochem Biophys Res Commun 2008; %19; 377(3):797-802.

(72) Decramer M, Rutten-van M M, Dekhuijzen P N et al. Effects of N-acetylcysteine on outcomes in chronic obstructive pulmonary disease (Bronchitis Randomized on NAC Cost-Utility Study, BRONCUS): a randomised placebo-controlled trial. Lancet 2005; 365(9470):1552-1560.

(73) Moretti M, Bottrighi P, Dallari R et al. The effect of long-term treatment with erdosteine on chronic obstructive pulmonary disease: the EQUALIFE Study. Drugs Exp Clin Res 2004; 30(4):143-152.

(74) Rahman I, Macnee W. Antioxidant pharmacological therapies for COPD. Curr Opin Pharmacol 2012; 12(3):256-265.

(75) Ichikawa T, Li J, Meyer C J et al. Dihydro-CDDO-trifluoroethyl amide (dh404), a novel Nrf2 activator, suppresses oxidative stress in cardiomyocytes. PLoS One 2009; 4(12):e8391.

(76) Pareek T K, Belkadi A, Kesavapany S et al. Triterpenoid modulation of IL-17 and Nrf-2 expression ameliorates neuroinflammation and promotes remyelination in autoimmune encephalomyelitis. Sci Rep 2011; 1:201.

(77) Jaquet V, Marcoux J, Forest E et al. NADPH oxidase (NOX) isoforms are inhibited by celastrol with a dual mode of action. Br J Pharmacol 2011; 164(2b):507-520.

(78) Churg A, Marshall C V, Sin D D et al. Late intervention with a myeloperoxidase inhibitor stops progression of experimental chronic obstructive pulmonary disease. Am J Respir Crit Care Med 2012; 185(1):34-43.

The invention claimed is:

1. A method for aiding in categorising or determining prognosis in a subject with Chronic Obstructive Pulmonary Disease (COPD), or in selecting a therapeutic strategy for a subject with COPD, or in monitoring disease progression or assessing effectiveness of a treatment regime for COPD, the method comprising:
obtaining a blood or serum sample from the subject, and
measuring the IgG or IgM antibody response to carbonylated vimentin in the sample obtained from the subject, wherein an increase in IgG or IgM antibody response relative to a control is a prognostic and predictive factor for COPD.

2. The method of claim 1 further comprising:
selecting a treatment regime making use of the information on the IgG or IgM antibody response to carbonylated vimentin in the sample.

3. The method of claim 1 wherein the step of measuring the IgG or IgM antibody response to carbonylated vimentin comprises: determining a ratio of IgG to IgM antibodies produced in the measured antibody response to carbonylated vimentin.

4. The method of claim 3 wherein if the ratio of IgG to IgM is low, the low IgG:IgM ratio being 4 or less or 3.5 or less, the subject has a lower probability of more advanced COPD (Global Initiative for Chronic Obstructive Lung Disease 2 (GOLD2) or Global Initiative for Chronic Obstructive Lung Disease 3 (GOLD3)) being present.

5. The method of claim 3 wherein if the ratio of IgG to IgM is high, the high IgG:IgM ratio being more than 4 or 4.5, 5 or more, or 6 or more, the subject has a higher probability of more advanced COPD (GOLD2 or GOLD3) being present.

6. The method of claim 3 further comprising:
selecting a treatment regime making use of the information on the IgG or IgM antibody response to carbonylated vimentin in the sample, wherein if the subject's anti-carbonylated vimentin IgG:IgM ratio is increased relative to control, then the selected treatment regime incorporates one or more of immunomodulatory treatment; antioxidant treatment; or carbonylation preventative treatment.

7. The method of claim 3 wherein a change in the anti-carbonylated vimentin IgG:IgM ratio for a COPD Global Initiative for Chronic Obstructive Lung Disease 1 (GOLD 1) subject from a "low" ratio, wherein the low ratio has an IgG:IgM ratio of 4 or less or 3.5 or less, to a "high" ratio, wherein the high ratio has an IgG:IgM ratio of more than 4 or 4.5, 5 or more, or 6 or more, provides an early indication of disease progression.

8. The method of claim 3 wherein a change in the anti-carbonylated vimentin IgG:IgM ratio for a COPD GOLD2 or GOLD3 subject from a "high" ratio, wherein the high ratio has an IgG:IgM ratio of more than 4 or 4.5, 5 or more, or 6 or more, to a "low" ratio, wherein the low ratio has an IgG:IgM ratio of 4 or less or 3.5 or less, provides an indication of disease improvement.

9. The method of claim 1 wherein the sample has been obtained from the subject as part of a clinical trial or as part of a monitoring programme.

10. The method of claim 1 wherein the step of measuring the IgG or IgM antibody response to carbonylated vimentin in the sample comprises:
performing an ELISA assay using a carbonylated vimentin polypeptide as the target polypeptide.

11. A method for treating a subject with Chronic Obstructive Pulmonary Disease (COPD), the method comprising:
administering to the subject an anti-idiotypic antibody or antibody fragment directed to an anti-carbonylated vimentin antibody; or a non-complement-activating anti-carbonylated vimentin antibody or antibody fragment.

12. A screening method for identifying a compound likely to be useful in treating Chronic Obstructive Pulmonary Disease (COPD), the method comprising:
determining the effect of a test compound on IgG or IgM antibody response to carbonylated vimentin in a sample from a subject receiving the test compound; and
selecting a compound that reduces said IgG or IgM antibody response relative to a control, reduces IgG:IgM antibody ratio relative to a control, or prevents or reduces an increase in IgG:IgM antibody ratio relative to a control.

* * * * *